United States Patent [19]

Hadley et al.

[11] Patent Number: 4,971,975

[45] Date of Patent: Nov. 20, 1990

[54] NOVEL COMPOUNDS

[75] Inventors: Michael S. Hadley; Paul A. Wyman; Barry S. Orlek, all of Harlow, England

[73] Assignee: Beecham Group plc, England

[21] Appl. No.: 182,139

[22] Filed: Apr. 15, 1988

[30] Foreign Application Priority Data

Apr. 15, 1987 [GB] United Kingdom ................ 8709025
Dec. 22, 1987 [GB] United Kingdom ................ 8729809
Feb. 24, 1988 [GB] United Kingdom ................ 8804224

[51] Int. Cl.$^5$ ................ C07D 471/08; A61K 31/435
[52] U.S. Cl. ................ 514/299; 540/582; 546/121; 548/131; 548/143; 548/235; 548/153
[58] Field of Search ................ 546/121; 514/299

[56] References Cited

U.S. PATENT DOCUMENTS 4,771,051  9/1988  Watsen ................ 514/267
4,797,387  1/1989  King ................ 514/212

FOREIGN PATENT DOCUMENTS 0307141   9/1988  European Pat. Off. ........... 514/299
0307142   9/1988  European Pat. Off. ........... 514/299
8607713   3/1986  United Kingdom ............... 514/299
8615784   6/1986  United Kingdom ............... 514/299
8622380   9/1986  United Kingdom ............... 514/299
8630896  12/1986  United Kingdom ............... 514/299
8721342   9/1987  United Kingdom ............... 514/299
8721343   9/1987  United Kingdom ............... 514/299
8801758   1/1988  United Kingdom ............... 514/299
8801759   1/1988  United Kingdom ............... 514/299
8812145   5/1988  United Kingdom ............... 514/299
8817311   7/1988  United Kingdom ............... 514/299

*Primary Examiner*—Robert Gerstl
*Attorney, Agent, or Firm*—Hopgood, Calimafde, Kalil, Blaustein & Judlowe

[57] ABSTRACT

A compound of formula (I) or a pharmaceutically acceptable salt thereof:

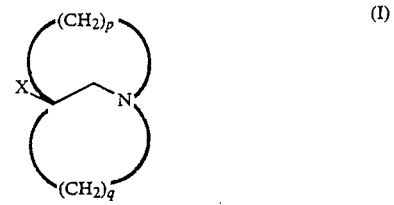

in which X represents $R_1OOC-$ in which $R_1$ is $C_{1-4}$ alkyl, $C_{2-4}$ alkenyl or $C_{2-4}$ alkynyl; $R_2O-$ in which $R_2$ is $C_{1-2}$ alkyl, $C_{1-2}$ alkylcarbonyl or aminocarbonyl optionally substituted by one or two methyl groups;
a group

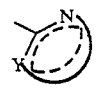

in which Y represents a 3-membered divalent residue completing a 5-membered aromatic ring and comprises one or two heteroatoms selected from oxygen, nitrogen and sulphur, any amino nitrogen optionally substituted by a $C_{1-2}$ alkyl group, Y being optionally C-substituted by a methyl group; or a group

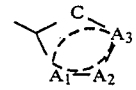

in which $A_1$ is oxygen or sulphur, one of $A_2$ and $A_3$ is $CR_3$ and the other is nitrogen or $CR_4$ where $R_3$ and $R_4$ are independently selected from hydrogen and methyl; and each of p and q independently represents an integer of 2 to 4.

12 Claims, No Drawings

COMPOUNDS

This invention relates to compounds having pharmaceutical activity, to a process for their preparation and their use as pharmaceuticals.

EP 0257741 and EP 0261763 disclose certain azabicyclic compounds which enhance acetylcholine function via an action at muscarinic receptors within the central nervous system.

A novel group of compounds has now been discovered which also enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

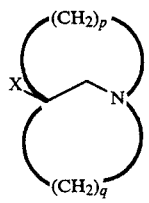

in which X represents $R_1OOC-$ in which $R_1$ is $C_{1-4}$ alkyl, $C_{2-4}$ alkenyl or $C_{2-4}$ alkynyl; $R_2O-$ in which $R_2$ is $C_{1-2}$ alkyl, $C_{1-2}$ alkylcarbonyl or aminocarbonyl optionally substituted by one or two methyl groups;
a group

in which Y represents a 3-membered divalent residue completing a 5-membered aromatic ring and comprises one or two heteroatoms selected from oxygen, nitrogen and sulphur, any amino nitrogen optionally substituted by a $C_{1-2}$ alkyl group, Y being optionally C-substituted by a methyl group; or a group

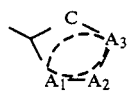

in which A1 is oxygen or sulphur, one of $A_2$ and $A_3$ is $CR_3$ and the other is nitrogen or $CR_4$ where $R_3$ and $R_4$ are independently selected from hydrogen and methyl; and each of p and q independently represents an integer of 2 to 4.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferably, p and q each independently represents 2 or 3. Most preferably p represents 2 and q represents 2 or 3.

Where X represents $R_1OOC-$ or $R_2O$, examples of alkyl moieties in X include methyl, ethyl, n- or iso-propyl, and n-, iso, sec- or tert - butyl. Preferably alkyl moieties in X are methyl or ethyl, most preferably methyl for $R_1$. Alkenyl or alkynyl moieties in X preferably have 2 or 3 carbon atoms, for example propargyl.

Preferably, where X is a 1,2,4-oxadiazolyl moiety, the ring carbon atom is methyl-substituted.

Preferably, any alkyl moiety in Y is methyl.

Suitable examples of X include methoxycarbonyl, ethoxycarbonyl, ethoxy, methylcarbonyloxy, aminocarbonyloxy, 3-methyl-1,2,4-oxadiazol-5-yl, 5-methyl-1,2,4-oxadiazol-3-yl, 1,3,4-oxadiazol-2-yl, 5-methyl-1,3,4-oxadiazol-2-yl, 1,3-oxazol-2-yl, 4-methyl-1,3-oxazol-2-yl, 5-methyl-1,3-oxazol-2-yl, 1,3-oxazol-4-yl, 2-methyl-1,3-oxazol-4-yl, 2-methyl-1,3-oxazol-5-yl, 1,2-oxazol-5-yl, 5-methyl-1,2-oxazol-3-yl, 1,3,4-thiadiazol-2-yl, 2-furyl and 5-methylfur-2-yl.

A subgroup of compounds within formula (I) is of formula (IA):

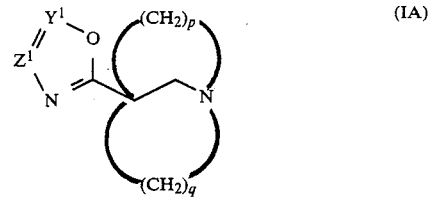

wherein one of $Y^1$ and $Z^1$ represents $CR_5$, where $R_5$ is hydrogen or methyl, or nitrogen, and the other represents $CR_6$ where $R_6$ is hydrogen or a methyl group, and the remaining variables are as defined in formula (I).

In compounds of formula (I) within formula (IA), suitable values for X include 3-methyl-1,2, 4-oxadiazol-5-yl, 5-(H or methyl)-1,3,4-oxadiazol-2-yl and 4-(H or methyl)-5-(H or methyl)1,3-oxazol-2-yl.

Examples of X are as described under formula (I).

Another subgroup of compounds within formula (I) is of formula (IB):

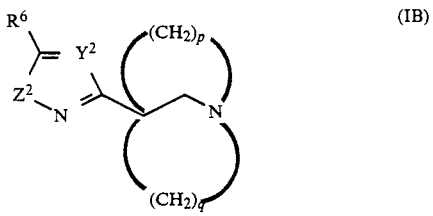

wherein $Y^2$ is nitrogen or CH, $Z^2$ is oxygen or $NR_7$ where $R_7$ is hydrogen or $C_{1-2}$ alkyl, and $R_6$ is hydrogen or methyl, and the remaining variables are as defined in formula (I).

In compounds of formula (I) within formula (IB), suitable values for X include 5-methyl-1, 2,4-oxadiazol-3-yl and 5-(H or methyl)-1,2-oxazol-3-yl.

Examples of X are as described under formula (I).

A further subgroup of compounds within formula (I) is of formula (IC):

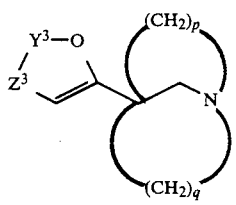

(IC)

wherein one of Y³ and Z³ is CR₃ and the other is CR₄, and R₃, R₄, p and q are as defined in formula (I).

In compounds of formula (I) within formula (IC), suitable values for X include 2-furyl and 5-methylfur-2-yl.

Suitable and preferred values for the remaining variables in formulae (IA), (IB) and (IC) are as described for the corresponding variables in formula (I).

The invention also provides a process for the preparation of a compound of formula (I), or a pharmaceutically acceptable salt thereof, which process comprises cyclising a compound of formula (II):

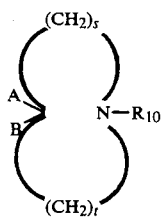

(II)

in which (i) A represents X or a group convertible thereto and B represents —(CH₂)ᵣL₁ where L₁ is a leaving group or A and L₁ together represent —COO—; one of r, s and t is 1 and the other two independently represent an integer of 2 to 4, and R₁₀ represents hydrogen or an N-protecting group; to give a compound of formula (IIa):

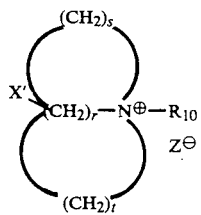

(IIa)

in which X' represents X or a group convertible thereto, Z— is an anion and the remaining variables are as previously defined;

or (ii) A represents an electron withdrawing group, B represents hydrogen and R₁₀ represents —(CH₂)ᵣ L₂ where L₂ is a leaving group; one of s and t is 1 and the other and r independently represent an integer of 2 to 4; to give a compound of formula (IIb):

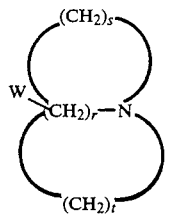

(IIb)

in which W represents an electron withdrawing group or X' and the remaining variables are as previously defined;

and thereafter, optionally or as necessary, removing any R₁₀ N-protecting group, converting W to X', converting X' to X, converting X to other X and/or forming a pharmaceutically acceptable salt.

The deprotection, conversion and interconversion steps may be carried out in any appropriate order.

Examples of the leaving groups L₁ and L₂ include halo such as bromo, tosyloxy and mesyloxy.

Examples of R₁₀ when an N-protecting group include benzyl and substituted benzyl.

Examples of A and X' when groups convertible to X include hydroxy, benzyloxycarbonyl and cyano.

The cyclisation reaction is a nucleophilic substitution which may be carried out under conventional conditions appropriate to the groups A and B. Thus, when B is (CH₂)ᵣBr and A is C₁₋₄ alkoxycarbonyl, the cyclisation is carried out in an inert solvent such as toluene or 4 ether at elevated temperature. When B is (CH₂)ᵣOTos or (CH₂)ᵣO-Mes, it is preferably obtained by treatment of a (CH₂)ᵣOH group with a suitable reagent such as tosylchloride or mesyl chloride, in a base such as pyridine, whereupon the cyclisation may proceed at ambient temperature, or at elevated temperature in an inert solvent such as toluene, and A is preferably hydroxy. When A and L₁ together represent —COO—, the cyclisation may be carried out in a lower alkanol such as ethanol in the presence of acid such as hydrogen bromide. In the resulting compound of formula (IIa), X' will be an alkoxycarbonyl group corresponding to the lower alkanol used for the cyclisation.

Where R₁₀ is an N-protecting group such as benzyl, this may be removed by conventional hydrogenation, preferably catalytically over a suitable catalyst such as Pd/C.

Examples of A when an electron withdrawing group include C₁₋₄ alkoxycarbonyl and cyano.

When A is an electron withdrawing group such as C₁₋₄ alkoxycarbonyl, B is hydrogen and R₁₀ is —(CH₂)ᵣL₂ where L₂ is, for example, chloro, the cyclisation may be effected by treatment of the compound of formula (II) with lithium diisopropylamide.

The conversion of W and X' may be carried out conventionally with regard to the group X.

Where X' is hydroxy, the intermediate alcohol may be converted into the desired compound of formula (I):

(i) where R₂ is alkyl, by etherification under conventional conditions, for example by reaction of the alcoholate anion (formed under basic conditions e.g. with sodium hydride) with a compound R₂L where L is a leaving group as halo e.g. bromo or iodo, in an inert solvent such as dimethylformamide. It may be necessary to protect the nitrogen atom with a suitable protecting group such as benzyl during the etherification, the group being subsequently removable by hydrogenation over a suitable catalyst such as Pd/C; (ii) where $R_2$ is alkylcarbonyl, by esterification under conventional conditions with the acid $R_2OH$ or suitable derivative thereof e.g. the acid anhydride, in a polar solvent such as dimethylformamide, or the acid or derivative itself acting as the solvent, at elevated temperature such as the boiling point of the solvent;

(iii) where $R_2$ is optionally substituted aminocarbonyl, by haloformylation with a suitable haloformate ester such as phenylhaloformate e.g. phenyl chloroformate, under basic conditions e.g. in the presence of pyridine, at depressed temperature, followed by nucleophilic substitution of the haloformate with the appropriate substituted amino in an inert solvent or the amine itself acting as the solvent, at ambient temperature.

Where X is a heterocyclic group as defined, it may be obtained from a W or X' group as described in, for example standard text books on heterocyclic chemistry such as 'Comprehensive Heterocyclic Chemistry', A. R. Katritzky and C. W. Rees, Pergamon, 1984.

The W or X' group is first converted, as necessary, to a suitable starting group X" for the chosen conversion reaction to give the required group X.

An X" carboxy group may be obtained by conventional de-esterification of an X' or W alkoxycarbonyl group. Where $R_{10}$ is an N-protecting group and X' or W is a benzyloxycarbonyl group, the de-esterification and deprotection steps may conveniently be effected simultaneously by conventional hydrogenation such as described above. Alternatively, an X" carboxy group may be obtained by conventional acid hydrolysis of an X' or W cyano group.

An X" chlorocarbonyl group may be obtained by treatment of an X" carboxy group with thionyl chloride at elevated temperature.

An X" aminocarbonyl group may be obtained by treatment of an X" chlorocarbonyl group with ammonia. Alternatively, an X" aminocarbonyl group may be obtained by partial alkaline hydrolysis of an X' or W cyano group, for example with an alkali metal hydroxide such as potassium hydroxide, in a polar solvent such as ethanol at elevated temperature. In some cases, it is preferable to carry out the partial hydrolysis using hydrogen peroxide and aqueous sodium hydroxide at room temperature. However, if this alternative procedure is adopted, the bridgehead nitrogen atom must be protected, preferably as a benzyl quaternary salt.

An X" cyano group may be obtained by treatment of an X" aminocarbonyl group with a dehydrating agent such as phosphorus pentoxide in toluene.

An X' or W cyano group may be converted to $CH_3CO-$ by treatment with methyl lithium in ether at depressed temperature. A $CH_3CO-$ group may alternatively be obtained by treatment of a LiOOC group with methyl lithium, the LiOOC group being obtained by hydrolysis of an X' or W alkoxycarbonyl group with lithium hydroxide in water.

An X' or W cyano or alkoxycarbonyl group may be converted to $-CHO$ by controlled reduction using a suitable reducing agent such as diisobutylaluminium hydride in an inert solvent such as toluene at low temperature.

An X" $-C(Q)=CH_2$ group where Q is halo such as chloro may be obtained by treatment of a $CH_3CO-$ group with an halogenating agent such as phosphorous pentachloride in chloroform at ambient temperature.

An X" $-C(Q)=CH_2$ group where Q is $OCOCH_3$ or $OSi(CH_3)_3$ may be obtained by treatment of a $CH_3CO-$ group with lithium diisopropylamide at low temperature, for example $-78°$ C., followed by reaction with acetylchloride or trimethylsilyl chloride.

An X" bromomethylcarbonyl group may be obtained by treatment of an X" $COCH_3$ group either with bromine in a suitable solvent such as methanol, the nitrogen of the azabicycle being protected as the hydrochloride salt, or with lithium diisopropylamide and trimethylsilyl chloride at low temperature followed by N-bromosuccinimide in tetrahydrofuran at low temperature. Alternatively, an X" $-COCl$ group may be converted to a $-COCH_2Br$ group by treatment with diazomethane in ether at low temperature followed by hydrogen bromide in acetic acid at ambient temperature.

An X" $CH_2N\equiv C$ group may be obtained from a formamidomethyl group by treatment with phosgene and triethylamine. The formamidomethyl group may in turn be obtained from the aminomethyl group by reaction with an ester of formic acid such as ethyl formate. The aminomethyl group may be obtained by reduction of the aminocarbonyl group with lithium aluminium hydride.

When X represents 3-methyl-1,2,4-oxadiazol-5-yl, an X" chlorocarbonyl group may be reacted with acetamide oxime, at elevated temperature in an inert, polar solvent such as chloroform, and the resulting substitution product cyclised at elevated temperature in a suitable solvent such as toluene or xylene. Alternatively, reaction of an X" aminocarbonyl group with an acetal of N,N-dimethylacetamide such as the dimethyl or diethyl acetal at elevated temperature yields an acyl amidine group $-CON=C(CH_3)N(CH_3)_2$ which may then be cyclised with hydroxylamine, in the presence of acid, such as acetic acid, which may also function as the solvent. The reaction may be carried out at ambient temperature, the N-hydroxy acyl amidine intermediate isolated and then cyclised at elevated temperature, or alternatively in a single step at elevated temperature.

When X represents 3-(H or methyl)-1,2,4-thiadiazol-5-yl, an X" aminocarbonyl group may be converted into an aminothiocarbonyl group using phosphorus pentasulphide or Lawesson's reagent (S. Scheibye, B. S. Pederson and J. O. Lawesson, Bull. Soc. Chim. Belg., 1978, 87 (3), 229). The aminothiocarbonyl may be converted into a thioacyl amidine group and cyclised as described above for the 1,2,4-oxadiazole group.

When X represents 5-methyl-1,2,4- oxadiazol-3-yl, an X" cyano group may be reacted with hydroxylamine, in a polar solvent such as methanol, to yield the corresponding amide oxime. The amide oxime may be cyclised using a suitable derivative of acetic acid such as the anhydride or a trialkylorthoacetate such as triethyl orthoacetate, the acid derivative acting as the solvent, at elevated temperature.

When X represents 5-(H or methyl)-1,3,4-oxadiazol-2-yl, an X" carboxy or carboxy ester group may be converted to the acid hydrazide by conventional procedures. For example, the acid may be converted to a $C_{1-6}$ alkyl ester e.g. methyl, with the appropriate $C_{1-6}$ alkanol e.g. methanol under conventional esterification conditions, and the resulting ester reacted with hydrazine at elevated temperature to give the acid hydrazide. The acid hydrazide may then be cyclised by condensation with a suitable derivative of the appropriate $C_{1-2}$ alkanoic acid $RCO_2H$, e.g. a trialkyl ortho-ester, such as the triethyl ortho-ester, the acid derivative acting as the solvent, at elevated temperature.

When X represents 5-(H or methyl)-1,3,4-thiadiazol-2-yl an X" acid hydrazide may be reacted with a suitable acylating agent such as methyl formate or an acetyl halide to give a diacyl hydrazide group, —CONHNH-COR which can be cyclised using phosphorus pentasulphide. The cyclisation is preferably carried out in the absence of solvent with the nitrogen of the azabicycle protected as the hydrochloride salt.

When X represents 1,3-oxazol-2-yl, the conversion may be effected by reaction of an X" aminocarbonyl group with vinylene carbonate at elevated temperature in the presence of a strong acid such as polyphosphoric acid, which may also function as the solvent.

When X represents 5-(H or methyl)-1,3-oxazol-2-yl, an X" carboxy group may first be converted to the carboxylic acid chloride and be reacted with a compound of formula $NH_2CH_2CR(OR')_2$, or the X" carboxy group may be reacted directly with the compound of formula $NH_2CH_2CR(OR')_2$ in the presence of a condensing agent such as dicyclohexylcarbodiimide or a chloroformate ester such as ethyl chloroformate, to give a group $CONHCH_2C(OR')_2R$; which may be cyclised using a suitable dehydrating agent such as polyphosphoric acid, phosphorus oxychloride, phosphorus pentachloride, sulphuric acid or sulphuryl chloride, preferably polyphosphoric acid.

An X 5-(H or methyl)-1,3-thiazol-2-yl group may be obtained by cyclisation of an X" —CONHCH$_2$-C(OR')$_2$R group using phosphorus pentasulphide. The reaction is preferably carried out in the absence of solvent with the nitrogen of the azabicycle protected as the hydrochloride salt.

1,3-Oxazol-2-yl groups 4-methyl-substituted may be provided by the cyclisation of an X" aminocarbonyl group with propargyl alcohol or acetate ester thereof, in the presence of a dehydrating agent such as polyphosphoric acid,using a catalyst such as $HgSO_4$, at elevated temperature.

Alternative routes to optionally 4-methyl-substituted 1,3-oxazol-2-yl groups include:

(i) the condensation of an X" aminocarbonyl group with the appropriate compound $BrCH_2COR$ at elevated temperature; or (ii) the reaction of an X" carboxy group under basic conditions with the appropriate compound $BrCH_2COR$ to give a group —$COOCH_2COR$ which may be cyclised with ammonium chloride.

Where R is hydrogen the aldehyde is preferably protected as an acetal.

During the reaction (i) above, the nitrogen atom of the bicyclic moiety may require protection.

When X is 4-(H or methyl)-1,3-thiazol-2-yl an X" aminothiocarbonyl group may be reacted with the appropriate α-halo acyl compound such as $BrCH_2COCH_3$ as indicated for the corresponding 1,3-oxazole. 1,3-Oxazol-4-yl groups optionally 2-substituted may be provided by reacting a bromomethylcarbonyl group with an appropriate $C_{1-2}$ alkanoic acid amide. Preferably, the reaction with acetamide is carried out at elevated temperature and the reaction with formamide is carried out in sulphuric acid.

An unsubstituted 1,3-oxazol-4-yl group may alternatively be obtained by treatment of an X" —$CH_2N\equiv C$ group with a formate ester such as methyl formate after deprotonation with a strong base such as n-butyl lithium or potassium t-butoxide.

When X represents 3-(H or methyl)-1,2-oxazol-5-yl, the reaction of an X" $CH_3CO$ group may be carried out at depressed temperature with ethyl formate or acetate in a suitable solvent such as toluene, under basic conditions such as sodium hydride and catalytic ethanol, followed by reflux, to yield the sodium salt of the dicarbonyl compound (IVa):

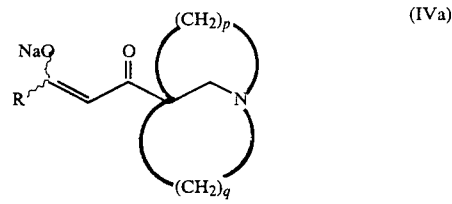

Subsequent cyclisation of the compound of formula (IVa) at ambient temperature with an aminating agent such as hydroxylamine-O-sulphonic acid in a dry solvent such as methanol, ethanol or diglyme, preferably in the presence of an acid such as sulphuric acid, p-toluene sulphonic acid or potassium hydrogen sulphate to minimise amination of the azabicycle, yields a compound of formula (I).

Alternatively, the compound of formula (IVa) may be treated prior to the cyclisation step with dimethylamine in ethanol in the presence of glacial acetic acid at ambient temperature to give the vinylogous amide (IVb):

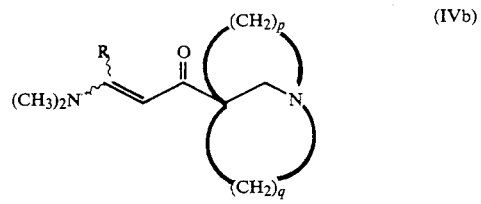

which may be cyclised as described above for the compound of formula (IVa).

When X represents a 3-substituted 1,2-oxazol-5-yl group, an X" —C(Q)=CH$_2$ group where Q is halo such as chloro, $OCOCH_3$ or $OSi(CH_3)_3$, may be treated with the nitrile oxide $CH_3C\equiv N^+$-$O^-$. The highly reactive nitrile oxide may conveniently be generated in situ from a halo oxime such as $CH_3C(Br)=NOH$ in a solvent such as N,N-dimethylformamide under basic conditions, either exploiting the basicity of the azabicyclic moiety or optionally with added base such as triethylamine. The halo oxime is prepared by treatment of $CH_3CH=NOH$ with a suitable halogenating agent such as N-bromosuccinimide in N,N-dimethylformamide at ambient temperature. Alternatively the nitrile oxide may be generated from the appropriate nitroalkane using a suitable dehydrating agent such as phenylisocyanate or phosphorous oxychloride in the presence of a base such as triethylamine in a suitable solvent such as chloroform, initially at depressed temperature followed by reflux.

When X represents an optionally 5-substituted 1,2-oxazol-3-yl group, an X" -C$\equiv$N$^+$-O$^-$ nitrile oxide group may be reacted with an olefin of the structure R-C(Q)=CH$_2$, where Q is halo such as chloro, $OCOCH_3$ or $OSi(CH_3)_3$ The highly reactive nitrile oxide may conveniently be generated in situ from an appropriate X" halo oxime —C(Br)=NOH by treatment with a base such as triethylamine in a solvent such as N,N-dimethylformamide. The halo oxime is prepared by treatment of an X" —CH=NOH oxime group with N-bromosuccinimide in N,N-dimethylformamide at ambient temperature, the azabicyclic being in the form of the hydrochloride salt. The X" —CH=NOH oxime group may be prepared from an X" —CHO group by reaction with hydroxylamine hydrochloride in a solvent such as methanol.

When X represents 1,3-oxazol-5-yl, the reaction of an X" —CHO group may be carried out by treatment with tosylmethylisocyanide in a hydroxylic solvent such as methanol, in the presence of a base such as potassium carbonate at elevated temperature.

When X represents a 2-(H or methyl)-1,3-oxazol-5-yl group, an X" —COCH$_2$Br group may be converted to —COCH$_2$NH$_2$ by treatment with NaN$_3$ in acetone or N,N-dimethylformamide followed by hydrogenation over a Pd/C catalyst in ethanolic HCl, or by treatment with hexamethylene tetramine followed by hydrolysis in methanolic HCl. The —COCH$_2$NH$_2$ group may then be acylated with the appropriate derivative of formic acid such as acetic-formic anhydride or acetic acid such as the anhydride or chloride to yield the acyl amino ketone (IVc):

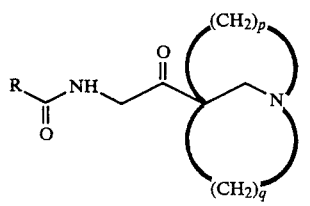
(IVc)

which can be cyclised using a suitable dehydrating agent such as polyphosphoric acid, sulphuric acid or phosphorous pentachloride at elevated temperature.

When X represents 2-furyl, an X" CHO group may be treated with a reactive derivative of propanal such as the 3-tosyl derivative and in which the carbonyl group is preferably protected as a cyclic acetal (V):

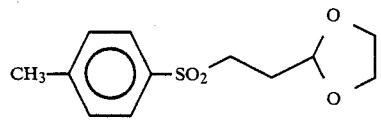
(V)

prepared by reaction of sodium 4-methylphenylsulphinate with 2-(2-bromoethyl)-1,3-dioxolane in dimethyl formamide at ambient temperature. The reaction of the compound of formula (V) with the X" —CHO group in an inert solvent such as tetrahydrofuran in the presence of a base such as n-butyl lithium, initially at low temperature, rising to ambient, yields a compound of formula (IVd):

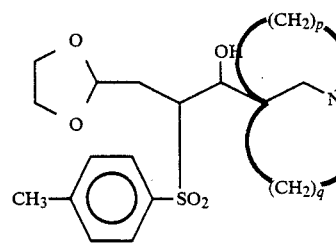
(IVd)

which may be cyclised at elevated temperature in the presence of an acid such as glacial acetic acid, which may also function as the solvent.

Alkyl-substituted furyl groups may be obtained analogously using the appropriately substituted analogue of the compound of formula (V) prepared from the corresponding ketone or aldehyde.

An X 1,3-thiazol-5-yl group may be obtained by dehydrating and cyclising a compound of formula (IVc) using phosphorous pentasulphide at elevated temperature.

Optionally 3-substituted 1,2-thiazol-5-yl groups may be prepared from the corresponding 1,2-oxazolyl group by ring opening effected by treatment with a reducing agent such as Raney nickel and hydrogen in a suitable solvent such as methanol or ethanol to yield a vinylogous amide of formula (IVe):

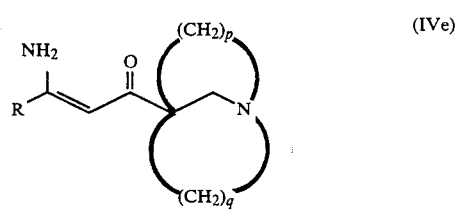
(IVe)

which may be cyclised using phosphorous pentasulphide in the presence of a suitable oxidising agent such as sulphur or chloranil in a solvent such as toluene at elevated temperature.

Compounds of formula (I) in which Y contains a sulphur atom in place of oxygen may be prepared analogously. A sulphur-containing group X" is obtained by treatment of a carbonyl-containing group X" with either phosphorus pentasulphide or with Lawesson's reagent (S. Scheibye, B. S. Pederson and S. O. Lawesson, Bull. Soc. Chim. Belg., 1978, 87(3), 229). The resulting sulphur-containing group X" may then be converted to the required sulphur-containing group X analogously to the conversion of carbonyl-containing groups. Where the thiolating agent is phosphorus pentasulphide, this may also effect cyclisation.

In the above description, R represents H or methyl and R' represents C$_{1-6}$ alkyl such as methyl or ethyl or two R' groups together represent C$_{2-6}$ polymethylene such as ethylene.

In formulae (IVa) to (IVe), the variables are as defined in formula (I).

Interconversion of X may be carried out conventionally. Thus, C$_{1-4}$ alkoxycarbonyl groups may be interconverted by acid hydrolysis to the intermediate carboxylic acid. The acid may be esterified by reaction with the appropriate alcohol R$_1$OH under acidic conditions at elevated temperature, to give the required group X. C$_{1-4}$ alkoxycarbonyl groups may also be converted to certain heterocyclic groups X as described above, either directly or via the intermediate carboxylic acid.

Compounds of formula (II) may be prepared conventionally.

Where A is C$_{1-4}$ alkoxycarbonyl, B is (CH$_2$)$_r$L$_1$ and R$_{10}$ is hydrogen or an N-protecting group, the compound of formula (II) may be prepared by treating a compound of formula (III).

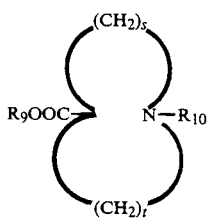

(III)

where $R_9$ is $C_{1-4}$ alkyl and the remaining variables are as previously defined, with lithium diisopropylamide, prepared in situ from diisopropylamine and n-butyllithium followed by reaction with a compound $L_3(CH_2)_rL_1$ where $L_3$ is a leaving group, in an inert solvent such as ether at depressed to elevated temperature. Both $L_1$ and $L_3$ are suitably bromo.

Where A and $L_1$ together represent —COO— and r is 2, the compound of formula (II) may be prepared by reacting the compound of formula (III), treated with lithium diisopropylamide as before, with ethylene oxide in an inert solvent such as ether at depressed to elevated temperature.

Where A and $L_1$ are each hydroxy and r is 3, the compound of formula (II) may be obtained by reduction of the corresponding compound of formula (II) where A and Ll together represent —COO— and r is 2 with $LiAlH_4$.

Where A and $L_1$ are each hydroxy and r is 1 or 2, the compound of formula (II) may be obtained by the reaction of a compound of formula (IV):

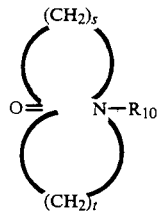

(IV)

with (a) cyanide ion, for example with potassium cyanide, followed by acid hydrolysis and reduction of the resulting carboxy group with, for example, $LiAlH_4$ to give the compound of formula (II) where r is 1; or (b) the carbanion $—CH_2CO_2C_2H_5$ generated by treating ethyl acetate with lithium diisopropylamide, followed by reduction of the resulting ethyl ester group with $LiAlH_4$ in an inert solvent such as ether, to give the compound of formula (II) where r is 2.

Where A is an electron withdrawing group such as $C_{1-4}$ alkoxycarbonyl, B is hydrogen and $R_{10}$ is $(CH_2)_rL_2$, the compound of formula (II) may be prepared by reacting the compound of formula (III) where $R_{10}$ is hydrogen with a compound $L_3(CH_2)_rL_2$ where $L_3$ is as previously defined, in a solvent such as acetone in the presence of a base such as potassium carbonate. The leaving group $L_3$ is preferably bromo and $L_2$ is preferably chloro.

Compounds of formulae (III) and (IV) are known compounds or may be prepared by analogous methods to those for preparing known compounds. The compound of formula (III) where s is 2 and t is 1 may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Novel compounds of the formulae (II), (IIa) and (IIb) also form part of this invention.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound. The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

Ethyl 1-benzyl-3-piperidylcarboxylate (D1)

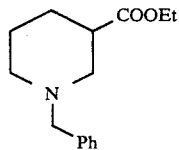

A solution of benzyl bromide (30.9 ml, 0.26 mole) in dry acetone (20 ml) was added dropwise over 20 min to a stirred mixture of ethyl 3-piperidylcarboxylate (39.0 ml, 0.25 mole) and anhydrous potassium carbonate (34.5 g, 0.25 mole) in dry acetone (300 ml). The mixture was stirred for a further 1 h at room temperature followed by 20 min at 45° C. The mixture was then filtered and the filtrate diluted with water, (250 ml) and extracted with ethyl acetate (3×200 ml). The combined extracts were dried (Na₂SO₄) and concentrated in vacuo to give an orange oil, which was extracted with n-pentane (2×200 ml). Concentration of the combined extracts gave the title compound (D1) as a yellow oil (50.2 g, 81%).

DESCRIPTION 2

Ethyl 1-benzyl-1-azoniabicyclo[3.3.1]non-5-ylcarboxylate bromide (D2)

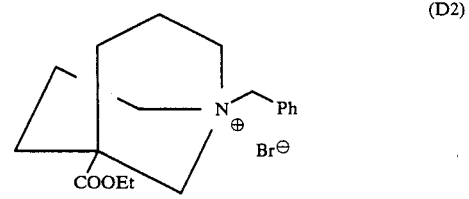

A solution of diisopropylamine (7.3 ml, 0.057 mole) in dry ether (130 ml) at −50° C. under nitrogen was treated with 1.55M n-butyllithium in hexane (29.0 ml, 0.045 mole). The solution was stirred for 15 min, then cooled to −65° C., treated with N,N,N',N'-tetramethylethylenediamine (14.6 ml) and stirred for a further 15 mins. A solution of ethyl 1-benzyl-3-piperidylcarboxylate (D1, 10.0 g, 0.040 mole) in dry ether (30 ml) was added dropwise over 10 min and the resulting solution stirred at −60° C. for 15 mins before the addition of 1,3-dibromopropane (4.4 ml, 0.045 mole). The reaction mixture was allowed to reach room temperature over 1h, followed by 40 min at reflux, before treating with saturated potassium carbonate solution (50 ml). The mixture was extracted with ether (3×70 ml) and the combined extracts dried (Na₂SO₄) and concentrated in vacuo to give an orange oil, which was dissolved in dry toluene (200 ml) and heated under reflux for 1h. The mixture was cooled and the precipitate which had formed was filtered off and dried, to give the title compound (D2) as a white solid (6.93 g, 47%) m.p. 183°–186° C.

DESCRIPTION 3

7-Benzyl-7-aza-2-oxaspiro[4,5]decan-1-one (D3)

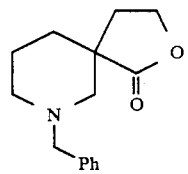

A solution of diisopropylamine (16 ml, 0.114 mole) in dry ether (200 ml) at −65° C. under nitrogen was treated with 1.6M n-butyllithium in hexane (64 ml, 0.102 mole) and the solution stirred for 15 mins, before treating with N,N,N',N'-tetramethylethylenediamine (30 ml). After stirring for a further 10 mins, the solution was treated dropwise over 10 mins with a solution of ethyl 1-benzyl-3-piperidylcarboxylate (D1, 20.5 g, 0.083 mole) in dry ether (50 ml) and stirring continued at −65° C. for 15 mins. Ethylene oxide (7.6 g, 0.17 mole) was then bubbled into the solution over 20 mins and the mixture was allowed to warm up to room temperature over 2 h followed by 40 min at reflux. The reaction mixture was treated with saturated sodium hydrogen carbonate solution (60 ml) and extracted with ether (3×120 ml). The combined extracts were dried (Na₂SO₄) and concentrated in vacuo to leave an orange oil. The unreacted starting material was removed by heating under reflux in 8M hydrochloric acid (100 ml) for 2 hours, followed by basifying to saturation with sodium hydrogen carbonate and extraction with ether. The organic extract was dried (Na₂SO₄) and concentrated in vacuo to leave an orange oil, which was distilled in the Kugelröhr apparatus (b.p. approx. 200° C.$_{0.4mm}$) to give the title compound (D3) as a yellow oil (12.1 g, 62%).

DESCRIPTION 4

Ethyl 1-benzyl-1-azoniabicyclo[3.2.1]oct-5-ylcarboxylate bromide (D4)

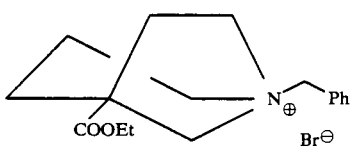

7-Benzyl-7-aza-2-oxaspiro[4,5]decan-1-one (D3, 11 g, 0.047 mole) was treated with a saturated solution of hydrogen bromide in ethanol (250 ml) and the mixture stirred at room temperature for 17 days. The mixture was concentrated in vacuo and the residue basified with saturated potassium carbonate solution, stirred for 10 mins and then extracted with chloroform (3×120 ml). The combined extracts were dried (Na₂SO₄) and concentrated in vacuo to give a brown oil, which consisted of a 1:1 mixture of the title compound (D4) with starting material (D3). This crude product was used in the next stage without purification.

DESCRIPTION 5

Ethyl (1-benzyl-3-hydroxy-3-piperidyl)acetate (D5)

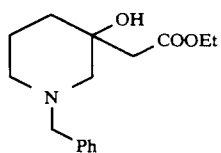

A solution of diisopropylamine (1.2 ml, 8.5 mmole) in dry ether (15 ml) at −50° C. under nitrogen was treated with 1.55M n-butyllithium in hexane (5.0 ml, 7.8 mmole). The solution was stirred for 15 min then cooled to −65° C. and treated with a solution of ethyl acetate (0.78 ml, 8.0 mmole) in dry ether (3 ml). This solution was stirred for a further 15 min and then treated dropwise over 10 mins with a solution of 1-benzyl-3-piperidone (1.48 g, 7.8 mmole) in dry ether (10 ml). The reaction mixture was stirred at −60° C. for 20 mins, then treated with 5M hydrochloric acid (5 ml) and allowed to reach room temperature, before basifying and saturating with potassium carbonate. The mixture was extracted with chloroform (3×60 ml), and the combined extracts dried (Na₂SO₄) and concentrated to leave a yellow oil. This was purified by passage through a silica gel column eluting with chloroform to give the title compound (D5) as a colourless oil (1.70 g, 79%).

DESCRIPTION 6

2-(1-Benzyl-3-hydroxy-3-piperidyl)ethanol (D6)

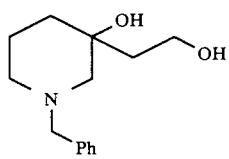

A solution of ethyl (1-benzyl-3-hydroxy-3-piperidyl)acetate (D5, 14.40 g, 0.052 mole) in dry ether (50 ml) was added dropwise over 15 min to a stirred suspension of lithium aluminium hydride (2.80 g, 0.075 mole) in dry ether (150 ml) at 0° C. under nitrogen. The reaction mixture was allowed to reach room temperature over 1 h and then heated under reflux for 40 mins. The mixture was then cooled in an ice bath and treated dropwise with water (2.8 ml), followed by 10% sodium hydroxide solution (8.4 ml), followed by water (2.8 ml). The inorganic solid was removed by filtration through a pad of Kieselguhr, washing well with ethyl acetate, and the filtrate was dried (Na₂SO₄) and concentrated to give the title compound (D6) as an orange oil (11.4 g, 93%). This was used without purification.

DESCRIPTION 7

1-Benzyl-5-hydroxy-1-azoniabicyclo3.2.1]octane chloride (D7a) and p-toluenesulphonate (D7b)

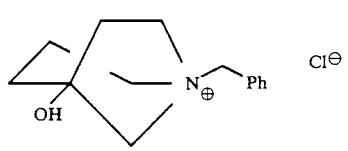

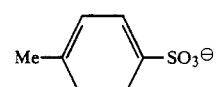

A solution of 2-(1-benzyl-3-hydroxy-3-piperidyl)ethanol (D6, 10.84 g, 0.046 mole) in pyridine (150 ml) at 0° C. was treated portionwise over 10 mins with p-toluenesulphonyl chloride (9.53 g, 0.050 mole) to give an orange solution, which was stored at about 8° C. for 16 h. The solid which crystallised out was then filtered off, washed well with ether and dried under vacuum to give the title compound (D7a) as a beige solid (7.36 g) m.p. 224°–227° C. The filtrate was then concentrated in vacuo and the residue partitioned between chloroform and saturated potassium carbonate solution. The organic layer was separated, dried (Na₂SO₄) and concentrated to leave a brown solid. This was recrystallised from acetone to give the p-toluenesulphonate (D7b) as a yellow solid (3.18 g). Total yield of 81%.

DESCRIPTION 8

1-Benzyl-5-ethoxy-1-azoniabicyclo[3.2.1]octane chloride (D8)

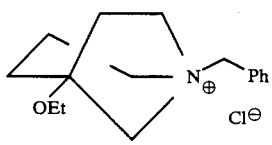
(D8)

A solution of 1-benzyl-5-hydroxy-1-azoniabicyclo-[3.2.1]octane chloride (D7a, 3.05 g, 0.012 mole) in dry DMF (100 ml) under nitrogen was treated with sodium hydride (600 mg of 80% oil dispersion, 0.020 mole) and stirred at room temperature for 40 min. The mixture was then treated with bromoethane (4.7 ml, 0.063 mole) and stirred at room temperature for 16 h. The excess sodium hydride was destroyed by addition of ethanol (5 ml) and the mixture acidified with glacial acetic acid (5 ml) and then concentrated in vacuo to give an orange semi-solid containing the title compound (D8). This was used in the next step without any purification.

DESCRIPTION 9

1-Azabicyclo[3.2.1]octan-5-ol (D9)

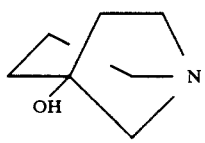
(D9)

A solution of 1-benzyl-5-hydroxy-1-azoniabicyclo-[3.2.1]octane chloride (D7a, 4.0 g, 0.017 mole) and p-toluenesulphonate (D7b, 3.10 g, 0.0080 mole) in ethanol (400 ml) was hydrogenated over 10% Pd/C (550 mg) at atmospheric pressure and 40° C. until the uptake of hydrogen ceased. The catalyst was filtered off through a pad of kieselguhr and the filtrate concentrated to leave a yellow solid. This was treated with saturated potassium carbonate solution (80 ml) and extracted with chloroform (3×100 ml). The organic extract was dried (Na$_2$SO$_4$) and concentrated to give the title compound (D9) as a white semi-solid (3.40 g), which was used in the next stage without further purification.

DESCRIPTION 10

Methyl 1-benzyl-2-oxo-4-pyrrolidylcarboxylate (D10)

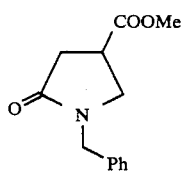
(D10)

A solution of dimethyl itaconate (50 g, 0.32 mole) in methanol (40 ml) was treated with benzylamine (34.6 ml, 0.32 mole) and the mixture heated under reflux for 2.5 h. The solution was then concentrated in vacuo and the residue purified by distillation (b.p. 162°–170° C.$_{0.2}$ mm) to give a pale yellow oil. This solidified on standing to give the title compound (D10) as a beige solid (66.2 g, 89%), m.p. 62°–63° C.

DESCRIPTION 11

Methyl 1-benzyl-3-pyrrolidylcarboxylate (D11)

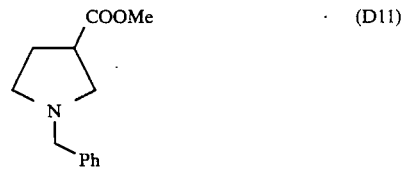
(D11)

A solution of methyl 1-benzyl-2-oxo-4-pyrrolidylcarboxylate (D10, 35.4 g, 0.18 mole) in dry THF (135 ml) was added dropwise over 30 mins to 1M borane-THF solution (228 ml, 0.23 mole) at 0° C. under nitrogen, and when addition was complete the solution was heated under reflux for 1 h. The solution was cooled to room temperature, then treated dropwise with 8% hydrogen chloride/methanol (114 ml, 0.25 mole HCl) and stirred for 18 h, followed by 3 h at reflux. The mixture was then concentrated in vacuo and the residue treated with water (40 ml), washed with ether (2×50 ml), basified with 40% sodium hydroxide solution, saturated with potassium carbonate and extracted with ether (3×70 ml). The combined extracts were dried (Na$_2$SO$_4$) and concentrated in vacuo to leave a yellow oil, which was purified by distillation (b.p. 146° C.$_{0.7}$ mm) to give the title compound (D11) as a colourless oil (19.8 g, 50%).

DESCRIPTION 12

7-Benzyl-7-aza-2-oxaspiro[4.4]nonan-1-one (D12)

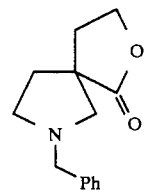
(D12)

Methyl 1-benzyl-4-pyrrolidylcarboxylate (D11, 7.50 g, 0.034 mole) was treated as in the method of DESCRIPTION 3 to give the crude product (D12) as an orange oil. This was distilled in a Kugelröhr apparatus (b.p. 190°–210° C.$_{0.2-0.5}$ mm) followed by column chromatography on silica gel eluting with ether, to give the title compound (D12) as a pale yellow oil (2.50 g, 36%).

DESCRIPTION 13

Ethyl 1-benzyl-1-azoniabicyclo[2.2.1]hept-4-ylcarboxylate bromide (D13)

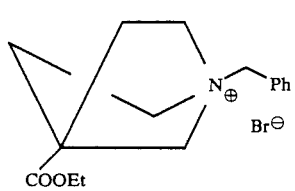
(D13)

7-Benzyl-7-aza-2-oxaspiro[4,4]nonan-1-one (D12, 2.5 g, 0.012 mole) was treated with a saturated solution of hydrogen bromide in ethanol (150 ml) and the resulting solution allowed to stand at room temperature for 3.5 days. The solution was concentrated in vacuo and the residue basified with saturated potassium carbonate solution, stirred for 10 mins and then extracted with chloroform (3×50 ml). The combined extracts were dried (Na₂SO₄) and concentrated in vacuo to give the title compound (D13) as a beige solid (3.40 g, 87%).

DESCRIPTION 14

1-Azabicyclo[3.3.1]non-5-ylcarboxylic acid hydrochloride salt (D14)

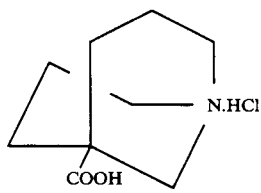

(D14)

A solution of ethyl 1-benzyl-1-azoniabicyclo[3.3.1]-non-5-ylcarboxylate bromide (D2, 7.90 g, 0.021 mole) in ethanol (150 ml) was hydrogenated over 10% Pd/C (700 mg) at atmospheric pressure and 40° C. until the uptake of hydrogen ceased. The reaction mixture was filtered through a pad of kieselguhr and the filtrate concentrated in vacuo to leave a yellow solid, which was treated with 8M hydrochloric acid (130 ml) and heated under reflux until TLC indicated that hydrolysis was complete. The solution was concentrated to dryness in vacuo to give the title compound (D14) as a yellow solid (4.8 g), which was used in the next stage without purification.

DESCRIPTION 15

1-Azabicyclo[3.2.1]oct-5-ylcarboxylic acid hydrochloride salt (D15)

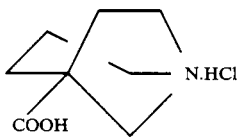

(D15)

The crude ethyl 1-benzyl-1-azoniabicyclo[3.2.1]oct-5-ylcarboxylate bromide (D4) was treated as in the method of Description 14 to give a yellow solid, consisting of a 1:1 mixture of the title compound (D15) and 7-benzyl-7-aza-2-oxaspiro[4,5]decan-1-one (D3). The crude product was purified by basifying with potassium carbonate solution, washing with chloroform (3×60 ml), re-acidifying with hydrochloric acid and concentrating in vacuo to give a yellow solid, which was heated under reflux in methanolic hydrogen chloride solution (140 ml) for 1.5 h. The mixture was filtered and the filtrate concentrated in vacuo to leave a yellow oil, which was basified with saturated potassium carbonate solution and extracted with chloroform (3×70 ml). The combined extracts were dried (Na₂SO₄) and concentrated to leave an orange oil, which was chromatographed on silica gel eluting with 10% methanol/chloroform to give a yellow oil (2.50 g). A sample of this material (1.10 g) was treated with 8M hydrochloric acid (80 ml) and heated under reflux for 24 h. The solution was concentrated in vacuo to give the title compound (D15) as a white solid (1.13 g).

DESCRIPTION 16

1-Azabicyclo[2.2.1]hept-4-ylcarboxylic acid hydrochloride salt (D16)

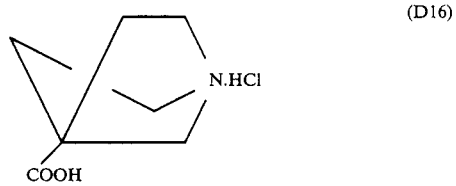

(D16)

Ethyl 1-benzyl-1-azoniabicyclo[2.2.1]hept-4-ylcarboxylate bromide (D13, 1.77 g, 0.0052 mole) was treated as in the method of Description 14 to give the title compound (D16) as a beige solid (0.96 g), which was used without purification.

DESCRIPTION 17

Acetamide Oxime (D17)

(D17)

A solution of sodium methoxide (prepared from 2.90 g, 0.126 mole of sodium) in methanol (50 ml) was added dropwise over 10 mins to a stirred solution of hydroxylamine hydrochloride (8.7 g, 0.126 mole) in methanol (100 ml). The mixture was stirred at room temperature for 1 h, then the precipitate was filtered off and the filtrate treated with acetonitrile (6.8 ml, 0.13 mole) and then heated under reflux. After 6 h, a further 6.8 ml of acetonitrile was added and reflux continued for a further 16 h. The solution was then concentrated in vacuo to give the title compound (D17) as a white solid (7.7 g, 83%), m.p. 123°–127° C.

DESCRIPTION 18

Ethyl 1-(2-chloroethyl)-3-piperidylcarboxylate (D18)

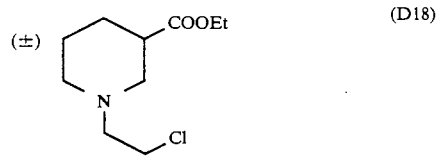

(D18)

A solution of ethyl 3-piperidylcarboxylate (100 g, 0.64 mole) in acetone (600 ml) was treated with 1-bromo-2-chloroethane (54 ml, 0.64 mole) and anhydrous potassium carbonate (138 g, 1.00 mole) and the mixture stirred at room temperature for 24 h. The mixture was concentrated in vacuo and the residue treated with water (400 ml) and extracted with ether (2×200 ml). The combined ether extracts were dried (Na₂SO₄) and concentrated in vacuo to leave a yellow oil, which was purified by chromatography on silica gel eluting with 50% ether/60–80 petrol to give the title compound (D18) as a pale yellow oil (50.0 g, 36%). ¹H Nmr (CDCl₃) δ

1.25 (3H, t, J=7Hz), 1.40–3.10 (11 H, m), 3.58 (2H, t, J=7Hz), 4.15 (2H, q, J=7Hz).

DESCRIPTION 19

5-Acetyl-1-azabicyclo[3.2.1]octane (D19)

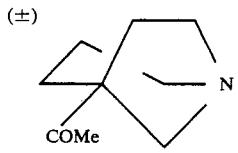

A solution of ethyl 1-azabicyclo[3.2.1]oct-5-ylcarboxylate (E7, Example 7 hereinafter, 6.0 g, 0.033 mole) in ethanol (20 ml) was treated with a solution of lithium hydroxide monohydrate (1.43 g, 0.034 mole) in water (60 ml). The mixture was stirred at room temperature for 18 h and then concentrated in vacuo to leave a white solid, which was dried thoroughly. A stirred suspension of this material (finely powdered) in dry THF (350 ml) under nitrogen was cooled to 0° C. and treated with methyllithium (30.0 ml of 1.4M solution in ether, 0.042 mole). The reaction mixture was heated under reflux for 5.5 h and then cooled to room temperature before adding to excess cold dilute hydrochloric acid. The aqueous mixture was basified with potassium carbonate solution and extracted with chloroform (3×100 ml). The combined extracts were dried (Na2SO4) and concentrated in vacuo to leave a yellow oil, which was purified by passage through a basic alumina column eluting with ethyl acetate, to give the title compound (D19) as a pale yellow oil (2.35 g, 45%).

$^1$H Nmr (CDCl$_3$) δ
5 1.45-1.55 (1H, m), 1.65-1.90 (4H, m), 2.00-2.10
(b 1M, m), 2.15 (3H, s), 2.65-3.00 (5H, m),
3.05-3.20 (1H, m).

Ir (film) υ C=O 1695 cm$^{-1}$.

DESCRIPTION 20

1-Azabicyclo[3.2.1]oct-5-ylcarboxamide (D20)

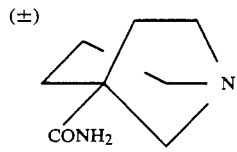

Ethyl 1-azabicyclo[3.2.1]oct-5-ylcarboxylate (E7, Example 7 hereinafter, 9.6 g, 0.053 mole) was treated with 8M hydrochloric acid (130 ml) and heated under reflux for 18 h. The solution was concentrated in vacuo to give a white solid, which was treated with thionyl chloride (80 ml) and heated under reflux for 6 h. The reaction mixture was concentrated in vacuo to leave a red semi-solid, which was suspended in dichloromethane (120 ml), cooled in an ice bath and treated with an excess of ammonia/dichloromethane solution. The mixture was stirred at room temperature for 1 h, then treated with saturated potassium carbonate solution. The organic layer was separated and the aqueous was extracted with chloroform (3×70 ml). All the organics were combined, then dried (Na2SO4) and concentrated in vacuo to give the title compound (D20) as a brown solid (6.2 g, 76%), which was used without further purification.

DESCRIPTION 21

1-Azabicyclo[3.2.1]oct-5-ylcarbonitrile (D21)

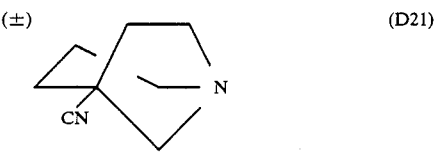

A stirred solution of 1-azabicyclo[3.2.1]oct-5-ylcarboxamide (D20, 2.20 g, 0.014 mole) in dry toluene (100 ml) was treated with phosphorus pentoxide (3.9 g, 0.028 mole) and heated under reflux for 7 h. The mixture was allowed to cool, basified with potassium carbonate solution and the toluene layer separated.

The aqueous was extracted with ether (2 x 60 ml) and the ether extracts combined with the toluene solution, dried (Na2SO4) and concentrated in vacuo to give the title compound (D21) as a yellow oil (1.6 g, 84%). This was used without further purification. $^1$H Nmr (CDCl$_3$)
1.40-1.55 (1H, m), 1.60-1.80 (1H, m), 1.85-2.20
(4H, m), 2.70-2.85 (2H, m), 2.85-3.00 (2H, m),
3.00-3.15 (2H, m)

DESCRIPTION 22

1-Azabicyclo[2.2.1]hept-4-yl carboxamide (D22)

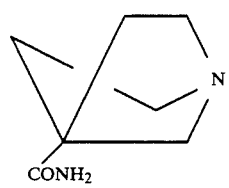

Ethyl 1-azabicyclo[2.2.1]hept-4-yl-carboxylate (E8, Example 8 hereinafter, 2 g, 0.012 mole) was converted by the procedures of description 20 to the crude title compound (D22, 1.33 g, 55%), used without further purification.

DESCRIPTION 23

1-Azabicyclo[3.2.1]oct-5-ylcarboxaldehyde (D23)

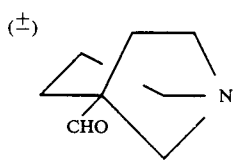

A solution of ethyl 1-azabicyclo[3.2.1]oct-5-yl- [-carboxylate (E7, Example 7 hereinafter, 6.0 g, 0.033 mole) in dry toluene (150 ml) at −65° C. under nitrogen was treated dropwise over 15 minutes with 1.5M diisobutylaluminium hydride in toluene (30 ml, 0.045 mole) and the reaction stirred at −65° C. for 1.25 h. The solution was poured into 10% sodium hydroxide solution (100 ml), stirred for 5 minutes and then extracted with ethyl acetate (1×150 ml) followed by chloroform (1 ×100 ml). The two extracts were dried (Na$_2$SO$_4$) and concentrated in vacuo separately. The ethyl acetate extract gave a gelatinous white semi-solid, which was shaken with ether (200 ml), filtered through a pad of kieselguhr and the filtrate concentrated in vacuo to leave a pale yellow oil. This was combined with the product from the chloroform extract to give a yellow oil (5.0 g) containing the title compound (D23), which was used without further purification.

DESCRIPTION 24

3-(4-Toluenesulphonyl)propanal ethylene acetal (D24)

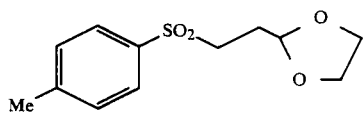

A mixture of sodium 4-toluenesulphinate monohydrate (37.2 g, 0 19 mole) and 2-(2-bromoethyl)-1,3-dioxolane (20 ml, 0.17 mole) in dry DMF (100 ml) was stirred at room temperature for 64 h, resulting in a homogenous solution. This was poured into ice/water (1 liter) containing conc. ammonia solution (100 ml) and stirred vigorously until a white precipitate formed. The solid was filtered off, washed with water, dried and recrystallised from propan-2-ol/ether to give the title compound (D24) as a white solid (28.7 g, 66%) m.p. 78–80° C.. $^1$H-NMR (CDCl$_3$) δ:
1.75–2.20 (2H, m), 2.42 (3H, s), 2.95–3.35 (2H, m), 3.70–3.95 (4H, m), 4.88 (1H, t, J=4Hz), 7.25 (2H, d, J=8Hz), 7.72 (2H, d, J=8Hz).

DESCRIPTION 25

4-(4-Toluenesulphonyl)butan-2-one ethylene ketal (D25)

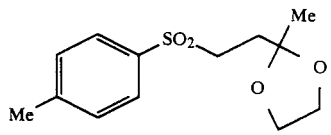

A stirred mixture of 4-toluenesulphinic acid (23.7 g, 0.15 mole) and ethylene glycol (30 ml) was treated over 10 minutes with methyl vinyl ketone (6.3 ml, 0.075 mole). The reaction was slightly exothermic and gave a clear solution. This was stirred at room temperature for 6 h, during which time a white precipitate formed. The mixture was poured into ice/water (600 ml) containing conc. ammonia solution (20 ml) and on vigorous stirring a white solid crystallised. This was filtered off, washed with water, dried and recrystallised from propan-2-ol/60–80 petrol to give the title compound (D25) as a white solid (15.2 g, 75%) m.p. 122–123° C. $^1$H-NMR (CDCl$_3$) δ:
1.27 (3H, s), 2.00–2.10 (2H, m), 2.45 (3H, s), 3.13–3.23 (2H, m), 3.80–3.95 (4H, m), 7.36 (2H, d, J=8Hz), 7.80 (2H, d, J=8Hz)

DESCRIPTION 26

2 1-Azabicyclo[3.2.1]oct-5-ylcarboxaldehyde oxime hydrochloride salt (D26)

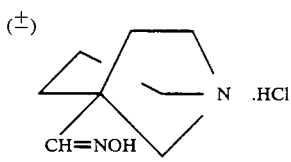

A solution of crude 1-azabicyclo[3.2.1]oct-5-ylcarboxaldehyde (D23, 2.11 g, assumed 0.0135 mole) in methanol (20 ml) was treated with hydroxylamine hydrochloride at room temperature overnight. After evaporation of the solvent in vacuo. the residue was diluted with water (50 ml), saturated with potassium carbonate and 3 extracted with chloroform (4 ×100 ml). The combined organic extracts were dried (Na$_2$SO$_4$) and concentrated to give the crude product. Chromatography on silica gel eluting with 15% methanol/chloroform yielded the desired product as a white crystalline solid (0.931 g) m.p. 108–110° C. which was converted to the hydrochloride and used without further purification.

DESCRIPTION 27

5-(α-Bromoacetyl)-1-azabicyclo[3.2.1]octane hydrobromide (D27)

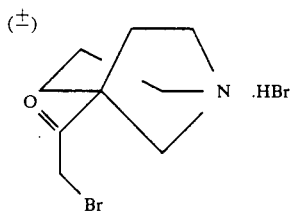

A Solution of the hydrobromide salt of 5-acetyl-1-azabicyclo[3.2.1]octane (D19) (2.0 g; 8.5 mmole) in dry methanol (35 ml) was cooled to −10° C. and treated with a solution of bromine (0.44 ml; 8.5 mmole) in dry methanol (5 ml). The reaction was maintained at 0° C. for 18 h. A further quantity of bromine (0.44 ml) was added and after 5 h at room temperature the reaction was diluted with water and stirred for 1 h. Evaporation of solvent and excess reagent in vacuo afforded a yellow foam (3.0 g) consisting mainly of the title compound (D27). This material was used in the next stage without purification.

Ir (film) vC=O 1720cm$^{-1}$

DESCRIPTION 28

5-(α-Azidoacetyl)-1-azabicyclo[3.2.1]octane (D28)

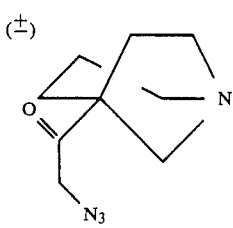

A solution of 5-(α-bromoacetyl)-1-azabicyclo[3.2.1]octane hydrobromide (D27) (1.8 g; 5.8 mmole) in dry N,N-dimethylformamide (25 ml) was treated with sodium azide (0.41 g; 6.3 mmole) and stirred in the dark at room temperature for 21 h. The reaction mixture was concentrated in vacuo and the residue was treated with a saturated potassium carbonate solution (25 ml) and extracted into chloroform (4×25 ml). The dried (sodium sulphate) organic layers were concentrated in vacuo to give the title compound (D28) as an orange oil (0.75 g; 67%) which was used in the next stage without purification.

Ir (film) $\nu N_3$ 2100 cm$^{-1}$

DESCRIPTION 29

5-α-(Acetylamino)acetyl]-1-azabicyclo[3.2.1]octane (D29)

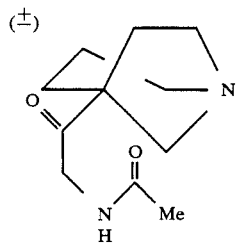

5-(α-Azidoacetyl)-1-azabicyclo[3.2.1]octane (D28) (0.35 g; 1.8 mmole) was hydrogenated for 5 h over a 5% Pd/C catalyst (0.2 g) in ethanol (30 ml) containing 1 ml of 36% hydrochloric acid. Filtration through Kieselguhr followed by evaporation of solvent in vacuo afforded the required amino ketone which was treated with absolute chloroform (30 ml) and acetyl chloride (0.26 ml); 3.6 mmole) followed by pyridine (0.29 ml; 3.6 mmole). The mixture was stirred vigorously at room temperature and after 1h a further portion of pyridine (0.29 ml) was added. Stirring was continued for an additional 3 h and during this period excess acetyl chloride (0.26 ml) and pyridine (0.29 ml) was added. The mixture was concentrated in vacuo and the residue was treated with saturated potassium carbonate solution (20 ml). Extraction into chloroform (4×20 ml) followed by drying (sodium sulphate) and evaporation in vacuo afforded a crude oil (0.4 g). Purification on neutral alumina using a graded eluant of 0–2% methanolchloroform afforded the title compound (D29) (0.13 g; 34%). $^1$H Nmr (CDCl$_3$) δ:

4 1.60–2.20 (6H, m), 2.04 (3H, s), 2.70–3.20 (6H, m), 4.25 (2H, m), 6.38 (1H, br, NH). 3C Nmr (CDCl$_3$) δ:
19.19, 23.00, 32.52, 33.93, 46.61, 52.22, 54.41, 54.82, 63.02, 170.16, 208.17.
Ir (film) $\nu$NH 3300cm$^{-1}$, $\nu$C=O 1710cm$^{-1}$, $\nu$C=O 1660cm$^{-1}$.

EXAMPLE 1

Ethyl 1-azabicyclo[3.3.1]non-5-ylcarboxylate (E1)

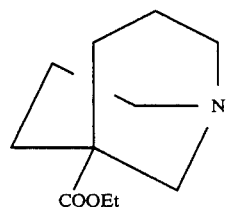

A solution of ethyl 1-benzyl-1-azoniabicyclo[3.3.1]-non-5-ylcarboxylate bromide (D2, 1.30 g, 0.0035mole) in ethanol (100 ml) was hydrogenated over 10% Pd/C (300mg) at atmospheric pressure and 40° C. until the uptake of hydrogen ceased. The reaction mixture was filtered through a pad of kieselguhr and the filtrate concentrated in vacuo to leave an orange solid, which was treated with saturated potassium carbonate solution (20 ml) and extracted with chloroform (3×40 ml). The combined extracts were dried (Na$_2$SO$_4$) and concentrated in vacuo to leave a yellow oil, which was distilled in a Kugelröhr apparatus (b.p. approx. 150° C.0.2mm) to give the title compound (E1) as a colourless oil (490mg, 71%). $^1$H Nmr (CDCl$_3$) δ:

1.24 (3H, t, J=7Hz), 1.45–1.59 (2H, m), 1.90–2.15 (6H, m), 2.94–3.10 (6H, m), 4.10 (2H, q, J=7Hz).
$^{13}$C Nmr (CDCl$_3$) δ:
14.19, 22.70, 31.91, 37.26, 51.72, 56.03, 60.27, 177.34.
M.S.: Calculated mass for C$_{11}$H$_{19}$NO$_2$=197.1416 Observed mass =197.1406.
Ir: (film) $\nu$C=O 1730cm$^{-1}$.

EXAMPLE 2

Methyl 1-azabicyclo[3.3.1]non-5-ylcarboxylate oxalate salt (E2)

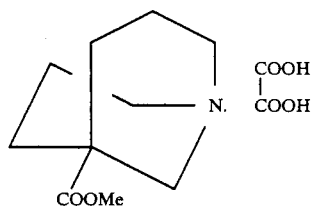

Ethyl 1-azabicyclo[3.3.1]non-5-ylcarboxylate (E1, 4.1 g, 0.021mole) was treated with 8M hydrochloric acid (130 ml) and the solution heated under reflux for 3 h. The solution was concentrated in vacuo to leave a yellow solid, which was dried thoroughly and then treated with methanolic hydrogen chloride solution and heated under reflux for 2 h. The solution was concentrated in vacuo and the residue basified with saturated potassium carbonate solution (40 ml) and extracted with chloroform (3×50 ml). The combined extracts were dried (Na₂SO₄) and concentrated to leave a yellow oil, which was distilled using a Kugelröhr apparatus (b.p. approx. 150° C.0.4mm) to give a white solid (2.8 g, 73%) m.p. 60–62° C. This was converted to the oxalate salt, which was recrystallised from methanol/ether to give the title compound (E2) as a 5 white solid m p. 122°–125° C.

Oxalate:- ¹H NMR (CD₃OD) δ:
1.84–2.06 (4H, m), 2.08–2.22 (2H, m), 2.30–2.52 (2H, m), 3.30–3.52 (6H, m), 3.71 (3H, s).

Analysis: $C_{10}H_{17}NO_2.C_2H_2O_4$ requires C: 52.75, H:7.00,

N: 5.15; found C: 52.40, H, 6.90, H: 4.95.

M.S.: Calculated mass for $C_{10}H_{17}NO_2 = 183.1259$
Observed mass = 183.1263.

EXAMPLE 3

Methyl 1-azabicyclo[3.2.1]oct-5-ylcarboxylate oxalate salt (E3)

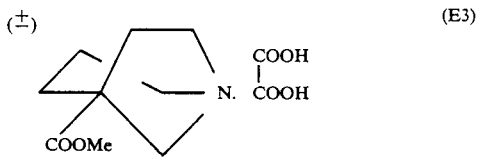

(E3)

A solution of the crude ethyl 1-benzyl-1-azoniabicyclo[-3.2.1]oct-5-ylcarboxylate bromide (D4) in ethanol (200 ml) and 11 M hydrochloric acid (5 ml), was hydrogenated over 10% Pd-C (1.0 g) at atmospheric pressure and 40° C. until the uptake of hydrogen was complete. The catalyst was filtered off through kieselguhr and the filtrate concentrated in vacuo to leave a yellow semisolid, which was treated with 8M hydrochloric acid (150 ml) and heated under reflux for 11 hours. The solution was concentrated to leave a yellow solid, which was basified with saturated potassium carbonate solution and washed with chloroform (3×60 ml). The aqueous solution was acidified with 11M hydrochloric acid and concentrated in vacuo to leave a yellow solid, which was heated under reflux in methanolic hydrogen chloride (140 ml) for 1.5 h. The mixture was filtered and the filtrate concentrated to leave a yellow oil, which was treated with saturated potassium carbonate solution and extracted with 8 chloroform (3×70 ml). The combined extracts were dried (Na₂SO₄) and concentrated in vacuo to give an orange oil, which was purified by column chromatography on silica gel eluting with 10% methanol/chloroform to give a yellow oil (2.50 g). This was converted into the oxalate salt and recrystallised from methanol/ether to give the title compound (E3) as a white solid m.p. 114°–116° C.

Oxalate:- ¹H Nmr (CD₃OD) δ:
1.90–2.25 (5H, m), 2.30–2.45 (1H, m), 3.20–3.40 (3H, m) 3.40–3.55 (1H, m), 3.55–3.70 (2H, m), 3.73 (3H, s).

Analysis: $C_9H_{15}NO_2 \cdot C_2H_2O_4$ requires C: 50.95H: 6.60,

N: 5.40; found C: 50.65, H: 6.95, N: 5.35.

M.S.: Calculated mass for $C_9H_{15}NO_2 = 169.1103$.
Observed mass=169.1101.

Free Base:—Ir (film): $\nu C=O$ 1730cm⁻¹.

EXAMPLE 4

5-Ethoxy-1-azabicyclo[3.2.1]octane hydrochloride salt (E4)

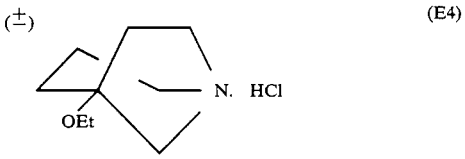

(E4)

A solution of the crude 1-benzyl-5-ethoxy-1-azoniabicyclo[3.2.1]octane chloride (D8) in ethanol (250 ml) was hydrogenated over 10% Pd.C (450mg) at atmospheric pressure and 40° C. until the uptake of hydrogen ceased. The catalyst was removed by filtration through a pad of kieselguhr and the filtrate concentrated to give a yellow solid. This was partitioned between chloroform and saturated potassium carbonate solution The 2 organic layer was separated, dried (Na₂SO₄) and concentrated to leave a yellow oil, which was distilled in a Kugelröhr apparatus (b.p. approx. 130° C.0.3mm) to give a colourless oil. This was converted to the hydrochloride salt, which was recrystallised from ethanol/ether to give the title compound (E4) as a hydroscopic white solid (1.25 g, 54%) m.p. 135°–137° C.

Hydrochloride:- ¹H Nmr (CD₃OD) δ:
1.17 (3H, t, J=7Hz), 1.84–2.20 (6H, m),
3.12–3.47 (5H, m), 3.48–3.62 (2H, m), 3.64–3.78 (1H, m).

M.S.: Calculated mass for $C_9H_{17}NO = 155.1310$
Observed mass = 155.1310.

EXAMPLE 5

1-Azabicyclo[3.2.1]oct-5-yl acetate hydrochloride salt (E5)

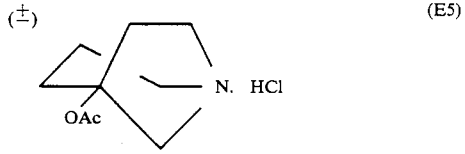

(E5)

1-Azabicyclo[3.2.1]octan-5-ol (D9, 1.20 g, 0.0094mole) was treated with acetic anhydride (20 ml) and heated under reflux for 15 minutes The solution was then concentrated in vacuo and the residue treated with saturated sodium hydrogen carbonate solution (40 ml) and 9 , extracted with chloroform (3×60 ml). The combined extracts were dried (Na₂SO₄) and evaporated to leave a yellow oil, which was distilled in a Kugelröhr apparatus (b.p. approx. 130° C.0 4mm) to give a colourless oil. This was converted into its hydrochloride salt and recrystallised from ethanol/ether to give the title compound (E5) as a white solid (1.05 g, 54%) m.p. 180°–182° C.

Hydrochloride:- 1H Nmr (CD₃OD) δ:
1.95–2.38 (5H, m), 2.05 (3H, s), 2.50–2.64 (1H, m), 3.20–3.48 (3H, m), 3.59 (2H, br.s), 3.63–3.77 (1H, m).

Analysis: $C_9H_{15}NO_2.HCl$ requires C: 52.55, H: 7.85, N:

6.80; found C: 52.20, H: 8.05, N: 6.80.

M.S.: Calculated mass for $C_9H_{15}NO_2 = 169.1103$

Observed mass=169.1102.
Free base:—Ir (film) υC=O 1740cm⁻¹.

EXAMPLE 6

Methyl 1-azabicyclo[2.2.1]hept-4-ylcarboxylate oxalate salt (E6)

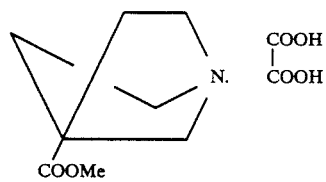

A solution of ethyl 1-benzyl-1-azoniabicyclo[2.2.1]-hept-4-ylcarboxylate bromide (D13, 3.40 g, 0.010 mole) in ethanol (150 ml) was hydrogenated over 10% Pd-C (500mg) at atmospheric pressure and 40° C. until uptake of hydrogen ceased. The catalyst was filtered off through a pad of kieselguhr and the filtrate concentrated in vacuo to leave a white solid, which was treated with 8M hydrochloric acid (70 ml) and heated under reflux for 10 h. The solution was concentrated in vacuo to leave an orange solid, which was dried thoroughly and then refluxed in methanolic hydrogen chloride (100 ml) for 2 hours. The solution was concentrated in vacuo and the residue basified with saturated potassium carbonate
solution, then extracted with chloroform (3×50 ml). The combined extracts were dried (Na₂SO₄) and concentrated to leave an orange oil, which was purified by column chromatography on silica gel eluting with 5% methanol/chloroform to give a yellow oil. This was converted to the oxalate salt and recrystallised from methanol/ether to give the title compound (E6) as a white solid (910mg, 37%), m.p. 131°-133° C.

Oxalate:- ¹H Nmr (CD₃OD) δ:
2.00-2.15 (2H, m), 2.30-2.45 (2H, m), 3.30-3.40 (2H, m), 3.42 (2H, s), 3.50-3.65 (2H, m), 3.76 (3H, s).

Analysis: $C_8H_{13}NO_2 \cdot C_2H_2O_4$ requires C: 49.00, H: 6.15,
N: 5.70; found C: 48.85, H: 6.20, N: 5.70.
M.S.: Calculated mass for $C_8H_{13}NO_2$=155.0946
Observed mass=155.0948.
Free Base:—Ir (film): υC=O 1730cm⁻¹.

EXAMPLE 7

Ethyl 1-azabicyclo[3.2.1]oct-5-ylcarboxylate (E7)

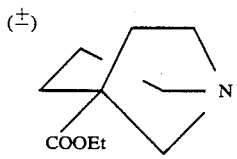

A solution of diisopropylamine (33.6 ml, 0.24 mole) in dry ether (1500 ml) at −65° C. under nitrogen was treated with 1.5M n-butyllithium in hexane (150 ml, 0.225 mole) and the solution stirred for 15 mins, before adding N,N,N',N'-tetramethylethylenediamine (68 ml, 0.45 mole). After stirring for a further 15 mins, the solution was treated with a solution of ethyl 1-(2-chloroethyl)-3-piperidylcarboxylate (D18, 44.7 g, 0.204 mole) in dry ether (100 ml) and the mixture allowed to warm up to room temperature over 2 h. The reaction mixture was treated with potassium carbonate solution (300 ml) and the ether layer separated, dried (Na₂SO₄) and concentrated in vacuo to leave an orange oil. This was purified by chromatography on silica gel eluting with 10% methanol/chloroform to give the title compound (E7) as a yellow oil (31.9 g, 84%), b.p. 120°-130° C.₀.₄ ₘₘ (Kugelröhr apparatus).

¹H Nmr (CDCl₃) δ:
1.25 (3H, t, J=7Hz), 1.10-2.20 (6H, m),
2.60-3.25 (6H, m), 4.20 (2H, q, J=7Hz).

EXAMPLE 8

Ethyl 1-azabicyclo2.2.1]hept-4-ylcarboxylate (E8)

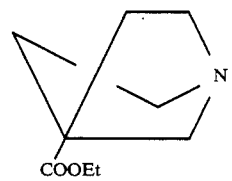

Ethyl 1-benzyl-1-azoniabicyclo[2.2.1]hept-4-ylcarboxylate bromide (D13, 15 g, 0.044 mole) in ethanol (250 ml) was hydrogenated over 10% Pd on carbon (1 g). The reaction was then filtered through celite and the filtrate concentrated in vacuo to yield the crystalline hydrobromide. The salt was partitioned between chloroform and saturated aqueous potassium carbonate solution. The organic phase was separated, dried, concentrated in vacuo and distilled to give the title compound (E8) as a colourless oil (7.7 g, 68%), b.p. 203°-205°/10 mm.

EXAMPLE 9

5-(3-Methyl-1,2,4-oxadiazol-5-yl)-1-azabicyclo[3.3.1]nonane oxalate salt (E9)

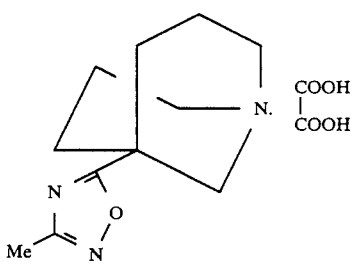

1-Azabicyclo[3.3.1]non-5-ylcarboxylic acid hydrochloride salt (D14) (1.79 g, 0.0087 mole) was treated with thionyl chloride (20 ml) and heated under reflux for 5 h. The solution was concentrated in vacuo to leave a white solid, which was taken up in chloroform (150 ml), treated with acetamide oxime (D17) (770mg, 0.0104 mole) and heated under reflux for 6 h. The reaction mixture was basified with saturated potassium carbonate solution and extracted with chloroform (3×80 ml). The combined extracts were dried (Na₂SO₄) and concentrated to leave a white solid, which was treated with xylene (200 ml) and heated under reflux for 1.5 h, using a Dean and Stark head to trap water formed. The reaction mixture was concentrated in vacuo to leave a yellow oil, which was chromatographed on silica gel eluting with 5% methanol/chloroform to give a colourless oil (1.60 g, 89%). This was converted to the oxalate salt and recrystallised from ethanol/ether to give the title compound (E9) as a white solid m.p. 168°–170° C.

Oxalate:—¹H NMR (d⁶-DMSO) δ:
1.75–1.90 (2H, m), 1.97–2.12 (2H, m), 2.15–2.25 (2H, m), 2.25–2.43 (2H, m), 2.35 (3H, s), 3.25–3.43 (4H, m), 3.47 (2H, s).

M.S.:—Calculated mass for $C_{11}H_{17}NO_3O = 207.1372$
Observed mass = 207.1371.

EXAMPLE 10

5-(3-Methyl-1,2,4-oxadiazol-5-yl)-1-azabicyclo[3.2.1]octane oxalate salt (E10)

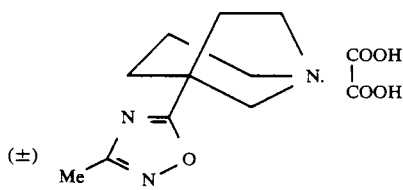

(E10)

1-Azabicyclo[3.2.1]oct-5-ylcarboxylic acid hydrochloride salt (D15) (1.24 g, 0.0065 mole) was treated as in the method of Example 9, to give the title compound as a white solid (720mg, 39%) m.p. 124°–127° C.

Oxalate:- ¹H NMR (CD₃OD) δ:
2.00–2.33 (4H, m), 2.37 (3H, s), 2.40–2.65 (2H, m), 3.35–3.48 (2H, m), 3.54–3.67 (2H, m), 3.69–3.86 (2H, m).

Analysis:- $C_{10}H_{15}N_3O.C_2H_2O_4$
requires C: 50.90, H: 6.05, N: 14.85
found C: 50.90, H: 5.90, N: 14.75.

M.S.: Calculated mass for $C_{10}H_{15}NO_3O = 193.1215$
Observed mass = 193.1214.

EXAMPLE 11

4-(3-Methyl-1,2,4-oxadiazol-5-yl)-1-azabicyclo[2.2.1]heptane oxalate salt (E11)

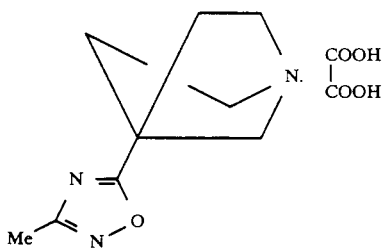

(E11)

1-Azabicyclo[2.2.1]hept-4-ylcarboxylic acid hydrochloride salt (D16) (960mg, 0.0052 mole) was treated as in the method of Example 9, to give the title compound as a white solid (350mg, 25%) m.p. 172°–174° C.

Oxalate:—¹H NMR (d⁶-DMSO) δ:
2.05–2.20 (2H, m), 2.27–2.43 (2H, m), 2.37 (3H, s), 3.20–3 35 (2H, m), 3.40–3.55 (2H, m), 3 42 (2H, s).

M.S.:—Calculated mass for $C_9H_{13}N_3O = 179.1059$
Observed mass = 179.1043.

EXAMPLE 12

5-(1,3-Oxazol-2-yl)-1-azabicyclo[3.2.1]octane oxalate salt (E12)

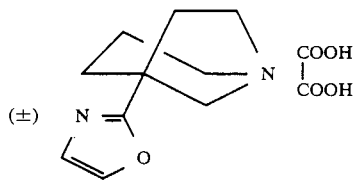

(E12)

A stirred mixture of 1-azabicyclo[3.2.1]oct-5-ylcarboxamide (D20, 1.50 g, 0.0097 mole) and vinylene carbonate (1.2 g, 0.014 mole) in polyphosphoric acid (35 g) was heated at 120°–130° C. for 2 h. The reaction mixture was allowed to cool, then treated with ice, before basifying with potassium carbonate solution. The aqueous was shaken well with ether, then the mixture filtered and the organic layer separated. The aqueous was again extracted with ether (2×80 ml) and all the ether extracts combined, dried (Na₂SO₄) and concentrated in vacuo to leave a yellow oil. This was chromatographed on a basic alumina column eluting with ethyl acetate and the material obtained converted to its oxalate salt and recrystallised from methanol/ether to give the title compound (E12) as a white solid (410mg, 16%) m.p. 143°–145° C.

Oxalate: ¹H Nmr (d6-DMSO) δ:
1.80–2.15 (4H, m), 2.20–2.45 (2H, m), 3.15–3.30 (2H, m), 3.35–3.65 (4H, m), 7.20 (1H, s), 8.13 (1H, s).

Analysis: $C_{10}H_{14}N_2O.C_2H_2O_4$ requires C: 53.75, H: 6.00, N: 10.45; found C: 53.80, H: 6.20, N: 10.25.

EXAMPLE 13

5-(2-Methyl-1,3,4-oxadiazol-5-yl)-1-azabicyclo3.2.1]octane oxalate salt (E13)

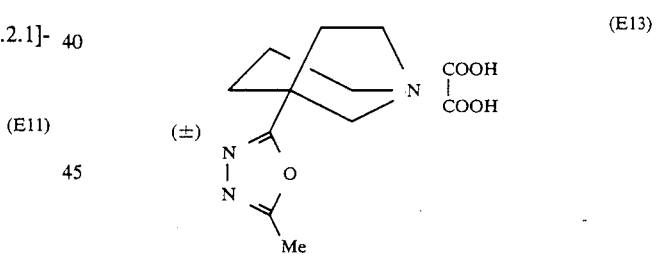

(E13)

Methyl 1-azabicyclo[3.2.1]oct-5-ylcarboxylate (E3, 1.25 g, 0.0074 mole) was treated with hydrazine hydrate (1.8 ml, 0.037 mole) and the mixture was heated at 120° C. for 2 h. The solution was allowed to cool, then treated with saturated potassium carbonate solution and extracted with chloroform (3×50 ml). The combined extracts were dried (K₂CO₃) and concentrated in vacuo to leave a yellow oil, which was treated with triethyl orthoacetate (8 ml) and heated at 120° C. for 2 h. The solution was then concentrated in vacuo, and the residue heated at 120° C. for a further 2 h. The reaction mixture was allowed to cool, then treated with saturated potassium carbonate solution and extracted using chloroform (3×70 ml). The combined extracts were dried (Na₂SO₄) and concentrated in vacuo to give a red oil, which was purified by column chromatography on basic alumina, eluting with 5% methanol/ethyl acetate to give a yellow oil (370 mg). This was converted into the oxalate salt, which was recrystallised from methanol/ether to give the title compound (E13) as a white solid (410mg, 20%) m.p. 153°-155° C.

Oxalate:- 1H Nmr (d6-DMSO) δ:
1.80-2.15 (4H, m), 2.25-2.45 (2H, m), 2.50 (3H, s), 3.20-3.30 (2H, m), 3.35-3.65 (4H, m)

Analysis: $C_{10}H_{15}N_3O.C_2H_2O_4$ requires C: 50.90, H: 6.05,

N: 14.85; found C: 50.80, H: 6.20; N: 14.75.

EXAMPLE 14

5-(1,3,4-Oxadiazol-2-yl)-1-azabicyclo[3.2.1]octane oxalate salt (E14)

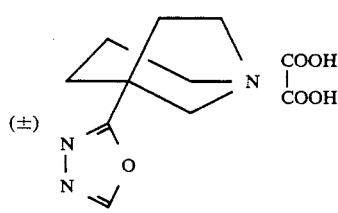

Ethyl 1-azabicyclo[3.2.1]oct-5-ylcarboxylate (E7) (2.0 g, 0.011 mole) was treated as in the method of Example 13, but using triethyl orthoformate in place of triethyl orthoacetate and an initial reaction time of 8 h at 120° C., followed by 2 h at 140° C. The crude product was purified by column chromatography on silica gel eluting with 20% methanol/chloroform to give a colourless oil. This was converted to its oxalate salt and recrystallised from methanol/ether to give the title compound (E14) as a white solid (270mg, 9%) m.p. 192°-194° C.

Oxalate:—$^1$H Nmr (d$^6$-DMSO) δ:
1.80-1.95 (1H, m), 1.95-2.20 (3H, m), 2.30-2.45 (2H, m), 3.20-3.30 (2H, m), 3.40-3.65 (4H, m), 9.30 (1H, s).

Analysis: $C_9H_{13}N_3O.C_2H_2O_4$ requires C: 49.05, H: 5.60,

N: 15.60; found C: 49.30, H: 5.80, N: 15.60.

EXAMPLE 15

5-(1,2-Oxazol-5-yl)-1-azabicyclo[3.2.1]octane oxalate salt (E15)

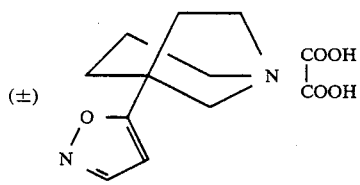

A solution of 5-acetyl-1-azabicyclo[3.2.1]Octane (D19, 2.30 g, 0.015 mole) in dry toluene (100 ml) was treated with ethyl formate (2.2 ml, 0.025 mole), sodium hydride (450mg of 80% oil dispersion, 0.015 mole) and ethanol (3 drops). The mixture was heated under reflux for 18 h, then cooled to room temperature and the precipitate filtered off and dried (2.30 g). This material suspended in ethanol (120 ml) and the mixture brought to pH6 by the addition of a 1M solution of p-toluenesulphonic acid in toluene. The resulting solution was treated with a solution of hydroxylamine-O-sulphonic acid (1.32 g, 0.012 mole) in ethanol (5 ml), stirred at room temperature for 1 h and then concentrated in vacuo. The residue was basified with saturated potassium carbonate solution and extracted with chloroform (3×80 ml). The combined extracts were dried (Na$_2$SO$_4$) and concentrated in vacuo to leave a yellow semi-solid, which was purified by column chromatography on silica gel eluting with 10% methanol/chloroform to give a colourless oil (550mg). This was converted to its oxalate salt and recrystallised from methanol/ether to give the title compound (E15) as a white solid (540mg, 13%) m.p. 122°-124° C.

Oxalate:- $^1$H Nmr (d6-DMSO) δ:
1.90-2.25 (4H, m), 2.35-2.45 (2H, m), 3.25-3.45 (2H, m), 3.50-3.75 (4H, m), 6.60 (1H, d, J=3Hz), 8.65 (1H, d, J=3Hz).

Free base:—Ir (film) υC=N 1585cm$^{-1}$.

Analysis: $C_{10}H_{14}N_2O.C_2H_2H_4$ requires C: 53.75, H: 6.00,

N: 10.45; found C: 54.00, H: 6.15, N: 10.50.

EXAMPLE 16

5-(5-Methyl-1,2,4-oxadiazol-3-yl)-1-azabicyclo3.2.1]octane oxalate salt (E16)

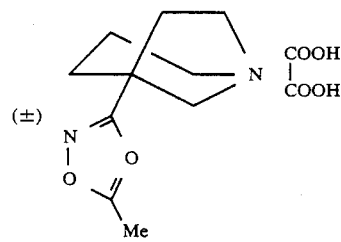

A solution of sodium methoxide in methanol (120 ml) (prepared from 1.04 g, 0.045 mole of sodium) was treated with hydroxylamine hydrochloride (3.05 g, 0.044 mole) and the mixture stirred at room temperature for 1.5 h. The mixture was filtered and the filtrate added to a solution of 1-azabicyclo[3.2.1]oct-5-ylcarbonitrile (D21, 1.50 g, 0.011 mole) in methanol (15 ml) and heated under reflux for 24 h. The solution was concentrated in vacuo to leave a white solid, which was treated with acetic anhydride (20 ml) and heated under reflux for 2 h, before concentrating in vacuo. The residue was basified with saturated potassium carbonate solution and extracted with ethyl acetate (3×70 ml). The combined extracts were dried (Na$_2$SO$_4$) and concentrated in vacuo to leave an orange oil, which was purified by chromatography on basic alumina, eluting with 10% ethyl acetate/ether to give a colourless oil. This was converted to its oxalate salt and recrystallised from methanol/ether to give the title compound (E16) as a white solid (310mg, 10%) m.p. 126°-127° C.

Oxalate:—$^1$H Nmr (d$^6$-DMSO) δ:
1.80-2.15 (4H, m), 2.20-2.40 (2H, m), 2.60 (3H, s) b 3.20-3.30 (2H, m), 3.35-3.65 (4H, m).

Analysis:- $C_{10}H_{15}N_3O.C_2H_2O_4$ requires C: 50.90, H: 6.05,

N: 14.85; found C: 50.90, H: 6.15, N: 14.75.

EXAMPLE 17

4-(2-Methyl-1,3,4-oxadiazol-5-yl)-1-azabicyclo[2.2.1]heptane oxalate salt (E17)

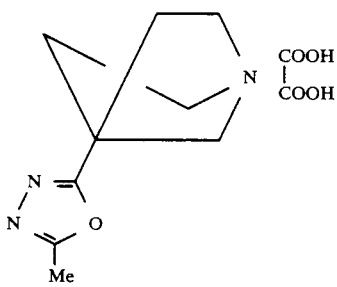

(E17)

Ethyl 1-azabicyclo[2.2.1]hept-4-yl carboxylate (E8, 1.2 g, 0.007 mole) was treated, by the procedures outlined in Example 13, with hydrazine hydrate followed by triethyl orthoacetate. Following the heating of the residue from the orthoacetate reaction at 120° for a further 2 h, the material was directly distilled to give an oil (0.8 g), b.p. 180°–185° C.0.1 mm. This was dissolved in ether (50 ml) and treated with oxalic acid (400mg) in methanol (2 ml). The precipitated oxalate salt was collected by filtration and recrystallised from methanol/ether to give the title compound (E17) as a white solid (1.08 g, 53%), m.p. 136°–138° C.

Oxalate:- $^1$H Nmr (d$^6$-DMSO) δ:

2.13 (2H, m, 3-H, 5-H), 2.43 (2H, m, 3-H, 5-H), 2.53 (3H, s, CH3), 3.33 (2H, m, 2-H, 6-H), 3.40

(2H, s, 7-CH2), 3.58 (2H, m, 2-H, 6-H).

Analysis:- C9H13N3O.C2H2O4 requires C: 49.00, H: 5.60,

N: 15.60; found C: 48.80, H: 5.50, N: 15.50.

EXAMPLE 18

4(1,3-Oxazol-2-yl)-1-azabicyclo2.2.1]heptane oxalate salt (E18)

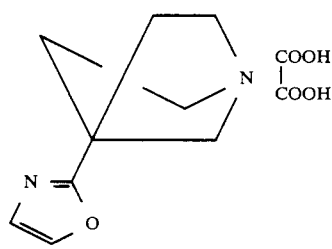

(E18)

1-Azabicyclo[2.2.1]hept-4-yl carboxamide (D22, 1.33 g, 0.0094 mole), was converted by the procedures described in Example 12, but using 5–10% methanol in ethyl acetate as eluant in the chromatographic purification. The title compound (E18) was obtained as a white solid (235mg, 8%), m.p. 174°–176° C.

Oxalate:—$^1$H Nmr (d$^6$-DMSO) δ:

2.25 (2H, m, 3-H, 5-H), 2.53 (2H, m, 3-H, 5-H), 3.5 (2H, m, 2-H, 6-H), 3.58 (2H, s, 7-CH2), 3.65 (2H, m, 2-H, 6-H), 7.42 (1H, s, 4'-H), 8.35 (1H, s, 5'-H).

EXAMPLE 19

4-(4-Methyl-1,3-oxazol-2-yl)-1-azabicyclo[2.2.1]heptane oxalate salt (E19)

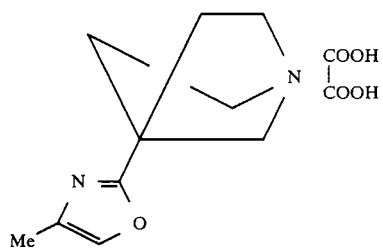

(E19)

To 1-azabicyclo[2.2.1]hept-4-yl carboxamide (D22, 1.33 g, 0.0094 mole) was added polyphosphoric acid (15 g), propargyl alcohol (0.64 ml) and mercuric sulphate (200mg) and the stirred mixture heated to 130° C. for 2 h. The reaction mixture was then poured into saturated aqueous potassium carbonate solution and the solution extracted exhaustively with ether to afford a yellow gum (450mg). To a solution of this gum in ether (20 ml) was added oxalic acid (250mg) in methanol (1 ml) and the resulting precipitate recrystallised from ether methanol to afford the title compound (E19, 490mg, 29%), m.p. 164°–166° C.

Oxalate:—$^1$H Nmr (d$^6$-DMSO) δ:

2.25 (2H, m, 3-H, 5-H), 2.29 (3H, s, 4'-CH3), 2.50 (2H, m, 3-H, 5-H), 3.50 (2H, m, 2-H, 6-H), 3.57 (2H, m, 7-CH2), 3.70 (2H, m, 2-H, 6-H), 8.05 (1H, s, 5'-H).

Analysis:- C10H14N2O.C2H2O4 requires C: 53.73, H: 6.10,

N: 10.40; found C: 53.80, H: 6.30, N: 10 70%.

EXAMPLE 20

4-(5-Methyl-1,3-oxazol-2-yl)-1-azabicyclo[2.2.1]heptane oxalate salt (E20)

(E20)

Ethyl 1-azabicyclo[2.2.1]hept-4-ylcarboxylate (E8, 1 g, 0.006 mole) was dissolved in 5N hydrochloric acid (30 ml) and heated under reflux overnight. The reaction mixture was then concentrated in vacuo to a gum which was dissolved in thionyl chloride (20 ml) and heated under reflux for 2 h. The thionyl chloride was then removed in vacuo to give the acid chloride as a crystalline solid. A solution of this in dry dichloromethane (15 ml) was treated with 1-aminopropan-2-one ethylene glycol ketall (0.65 g) and dry pyridine (0.7 g) in dichloromethane (10 ml) and the reaction was stirred at room temperature for 9 h. The solution was then concentrated in vacuo to a gum which was dissolved in polyphosphoric acid (25 g) and warmed from 120° to 160° C. over 30 mins and kept at this temperature for 1 h. The reaction was then cooled and poured into saturated aqueous potassium carbonate solution and the product recovered by extraction into ether. The organic extract was chromatographed on alumina in a gradient of 5–15% methanol in ethyl acetate to afford as the main fraction eluting in 10% methanol in ethyl acetate the required oxazole (250mg). A solution in ether (10 ml) was treated with oxalic acid (140mg) in methanol (0.5 ml) and the precipitate recrystallised from ether/methanol to afford the title compound (E20, 270mg), m.p. 144°–146° C.

Oxalate: 1H Nmr (d6-DMSO) δ:
2.04 (2H, m, 3-H, 5-H), 2.30 (2H, m, 3-H, 5-H),
2.32 (3H, s, 5'-CH3), 3.26 (2H, m, 2-H, 6-H),
3.36 (2H, s, 7-CH2), 3.50 (2H, m, 2-H, 6-H),
6.85 (1H, s, 4'-H)

Analysis: $C_{10}H_{14}N_2O \cdot C_2H_2O_4$ requires C: 53.70, H: 6.10,
N: 10.40; found C: 53.20, H: 6.00, N: 10.20.

1. Jiro Adachi and Nobuhiro Sato, J. Org. Chem. 1972, 37 221.

EXAMPLE 21

5-(Fur-2-yl)-1-azabicyclo[3.2.1]octane hydrochloride salt (E21)

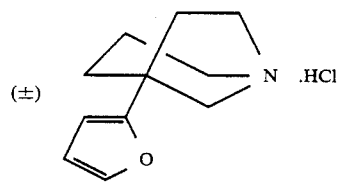

(E21)

(±)

A solution of 3-(4-toluenesulphonyl)propanal ethylene acetal (D24, 4.1g, 0.016 mole) in dry THF (120 ml) at 0°–65° C. under nitrogen was treated with 1.6M n-butyllithium in hexane (10 ml, 0.016 mole) and stirred for 10 minutes. This solution was treated with a solution of crude 1-azabicyclo[3.2.1]oct-5-ylcarboxaldehyde (D23, 2.5 g, assumed 0.016 mole) in dry THF (40 ml) and the reaction mixture allowed to warm up to room temperature over 1.5 h. The solution was treated with conc. potassium carbonate solution (150 ml) and then concentrated in vacuo to about half the volume, before extracting with chloroform (3×100 ml). The combined extracts were dried (Na2SO4) and concentrated in vacuo to leave an orange oil (8.1 g), which was dissolved in glacial acetic acid (250 ml) and heated under reflux for 48 h. The solution was concentrated in vacuo. the residue basified with saturated potassium carbonate solution and extracted with chloroform (2×100 ml). The combined extracts were dried (Na2SO4) and concentrated in vacuo to give a dark brown oil, which was chromatographed initially on basic alumina eluting with ether and then on silica gel eluting with 0 to 25% methanol/chloroform. The yellow oil was distilled using a Kugelröhr apparatus (b.p. 160° C. at 0.2mm) to give a colourless oil, which was converted to its hydrochloride salt and recrystallised from methanol/ether to give the title compound (E21) as a white solid (350 g, 10%) m.p. 176°–178° C.

Hydrochloride:—1H-NMR (d6-DMSO) δ:
2 1.80–2.35 (6H, m), 3.15–3.65 (6H, m), 6.30 (1H, m), 6.43 (1H, m), 7.63 (1H, m).

Analysis;- $C_{11}H_{15}NO \cdot HCl$ requires C: 61.80, H: 7.55, N:
6.55; found C: 61.85, H: 7.40, N: 6.45.

EXAMPLE 22

5-(5-Methylfur-2-yl)-1-azabicyclo[3.2.]octane hydrochloride salt (E22)

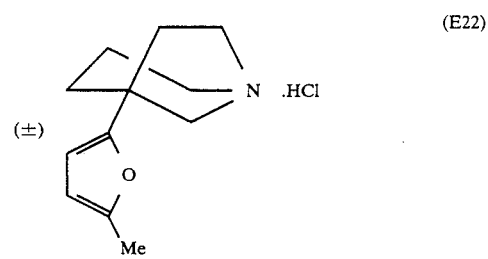

(E22)

(±)

A stirred suspension of 4-(4-toluenesulphonyl)-butan2-one ethylene ketal (D25, 4.32 g, 0.016 mole) in dry THF (150 ml) at −65° C. under nitrogen was treated with 1.6M n-butyllithium in hexane (10 ml, 0.016 mole) and the mixture allowed to warm up gradually until a homogenous solution was obtained (about −10° C.). The solution was cooled back to −65° C. and treated with a solution of crude 1-azabicyclo[3.2.1]oct-5-ylcarboxaldehyde (D23, 2.5 g, assumed 0.016 mole) in dry THF (40 ml). The reaction mixture was allowed to warm to room temperature over 1.5 h, then treated with potassium carbonate solution (100 ml); concentrated in vacuo to about a third of its volume and extracted with chloroform (3×100 ml). The combined extracts were dried (Na2SO4) and concentrated in vacuo to leave a yellow solid (8.9 g), which was dissolved in glacial acetic acid (250 ml) and heated under reflux for 16 h. The solution was concentrated in vacuo, the residue basified with saturated potassium carbonate solution and extracted with chloroform (2×100 ml). The combined extracts were dried (Na2SO4) and concentrated in vacuo to leave a brown oil, which was chromatographed initially on basic alumina eluting with ethyl acetate and then on silica gel eluting with 0 to 20% methanol/chloroform. The yellow oil was distilled in a Kugelröhr apparatus (b.p. 160°–170° C. at 0.15 mm) to give a colourless oil, which was converted to its hydrochloride salt and recrystallised from methanol/ether to give the title compound (E22) as a white solid (330mg, 9%) m.p. 182°–184° C.

Hydrochloride:—1H-NMR (d6-DMSO) δ:
1.75–2.30 (6H, m), 2.23 (3H, s), 3.15–3.60 (6H, m), 6.02 (1H, m), 6.15 (1H, s).

Analysis:—$C_{12}H_{17}NO \cdot HCl$ requires C: 63.30, H: 7.95, N:
6.15; found C: 63.05, H: 7.85, N: 5.90.

EXAMPLE 23

5-(5-Methyl-1,2-oxazol-3-yl)-1-azabicyclo[3.2.1]octane hydrochloride salt (E23)

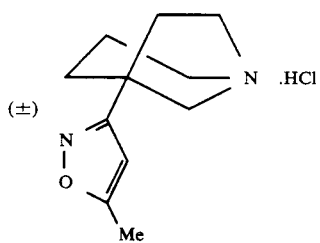
(±)         (E23)

N-Bromosuccinimide (1.01 g, 0.0057 mole) was added portionwise over 30 min to a solution of 1-azabicyclo[3.2.1]oct-5-ylcarboxaldehyde oxime hydrochloride salt (D26, 0.982 g, 0.0052 mole) in DMF (50 ml) at room temperature. After complete addition the mixture was stirred at room temperature for 1.5 h before cooling to −15° C. 2-Chloropropene (5.6 ml, 0.065 mole) was added in a single portion followed by dropwise addition of triethylamine (2.15 ml, 0.0155 mole) in DMF (15 ml) over 4 h, maintaining the temperature below −10° C. throughout. The reaction mixture was stirred for 1 h at 0° C., warmed to room temperature and evaporated in vacuo. The residue was diluted with water (30 ml), saturated with potassium carbonate and extracted with chloroform (4×50 ml). The combined extracts were dried ($Na_2SO_4$) and concentrated in vacuo to give a brown oil which was chromatographed on silica using 12% methanol/chloroform as eluant to give a white crystalline solid (0.178 g) m.p. 68°–69° C. This was converted to its hydrochloride salt and recrystallised from methanol/acetone to yield the title compound (E23) as a white solid (0.198 g, 17%) m.p. 223°–225° C. (dec).

Hydrochloride:—$^1$H-NMR (d$^6$-DMSO) δ:
1.85–2.35 (6H, m), 2.46 (3H, s), 3.25–3.70 (6H, m), 6.41 (1H, s).
$^3$C NMR (d$^6$ DMSO) δ:
11.81, 16.71, 31.91, 33.04, 41.93, 49.74, 51.31, 59.14, 100.13, 165.41, 169.88.
Free base:—Ir (film) 1740, 1600cm$^{-1}$.

EXAMPLE 24

5-(1,3,4-Thiadiazol-2-yl)-1-azabicyclo[3.2.1]octane oxalate salt (E24)

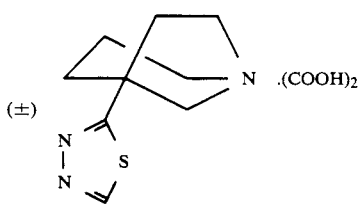
(±)         (E24)

Ethyl-1-azabicyclo[3.2.1]oct-5-ylcarboxylate (E7, 2.0 g, 0.011 mole) was treated with hydrazine hydrate (2.7 ml, 0.055 mole) as in the method of Example 13 to give the crude hydrazide (2.2 g) as an oil. This product was refluxed in a mixture of methyl formate (15 ml) and methanol (5 ml) for 16 h. The cooled reaction mixture was evaporated in vacuo to give the crude diacylhydrazide which was converted to the hydrochloride salt (2.95 g). An intimate mixture of this salt and phosphorus pentasulphide (12 g, 0.027 mole) was heated to 200° C. over 0.75 h and then maintained at this temperature for a further 0.75 h. The reaction mixture was cooled and diluted with water (75 ml), rendered basic with potassium carbonate and stirred for 1 h. The solution was then saturated with potassium carbonate and extracted with chloroform (4×100 ml). The combined organic extracts were dried ($Na_2SO_4$) and evaporated in vacuo. The residual oil was chromatographed on silica gel eluting with 10% methanol/chloroform to give the thiadiazole as a crystallising oil (0.644 g). This was converted to its oxalate salt and recrystallised from methanol/acetone to yield the title compound (E24) as a white solid (0.644 g, 21%) m.p. 177°–179° C.

Oxalate:—$^1$H-NMR (d$^6$-DMSO) δ:
2 1.80–2.00 (1H, m), 2.00–2.20 (3H, m), 2.30–2.45 (2H, m), 3.15–3.30 (2H, m), 3.35–3.65 (4H, m), 9.62 (1H, s).
$^{13}$C NMR (d$^6$-DMSO) δ:
17 39, 34.33, 35.65, 45.26, 49.99, 51.61, 61.01, 154.17. 164.81. 172.35.
Free base:—Ir (film) 1450, 1400cm$^{-1}$.
M.S.: Calculated mass for $C_9H_{13}N_3S = 195.08301$
Observed mass = 195.0828.

EXAMPLE 25

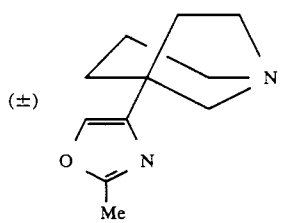
(±)         (E25)

A mixture of 5-(α-bromoacetyl)-1-azabicyclo[3.2.1]octane hydrobromide (D27) (0.31 g; 1.0 mmole) and acetamide (0.12 g; 2.0 mmole) was heated under nitrogen to 160° C. over a period of 30 min and then maintained at this temperature for 30 min. The reaction was treated with water (10 ml), saturated with potassium carbonate and extracted into chloroform (4×15 ml). The dried (sodium sulphate) organic layers were concentrated in vacuo. Purification on neutral alumina using chloroform as eluant afforded the title compound (E25) as a colourless oil (0.12 g; 63%).

$^1$H Nmr (CDCl$_3$) δ:
1 1.30–2.20 (6H, m), 2.40 (3H, s), 2.50–3.20 (6H, m), 7.14 (1H, s).
Ir (film) υC=N 1580cm$^{-1}$.

EXAMPLE 26

5-(2-Methyl-1,3-oxazol-5-yl)-1-azabicyclo[3.2.1]octane (E26)

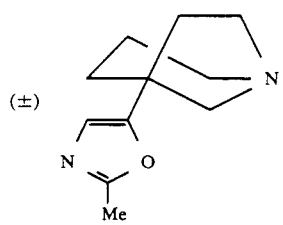
(±)         (E26)

A mixture of 5-[α-(acetylamino)acetyl]-1-azabicyclo[3.2.1]octane (D29) (0.12 g, 0.57 mmole) and polyphosphoric acid (6.0 g) under nitrogen was placed in an oil bath at 110° C. and heated to 160° C. over a period of 15 min. The temperature was maintained at this level for a further 15 min and the reaction was then poured onto ice. After basifying with 40% sodium hydroxide the solution was saturated with potassium 5 carbonate and extracted into chloroform (4×20 ml). Concentration of the dried (sodium sulphate) organic layers followed by purification on neutral alumina using a graded eluant of 5-10% methanol in ethyl acetate afforded the title compound (E26) as a colourless oil (40mg; 36%).

$^1$H Nmr (CDCl$_3$) δ:
1.45-2.20 (6H, m), 2.40 (3H, s), 2.63-3.25 (6H, m), 6.52 (1H, s).
Ir (film) υC=N 1575cm$^{-1}$.

BIOLOGICAL ACTIVITY

Radio ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1ml aliquots at −20° C.

Incubations (total volume 2 ml) are prepared using the above buffer with the addition of 2 mM magnesium chloride in the 3H—Oxotremorine—M (3H—OXO—M) experiments. For 3H—Quinuclidinyl Benzilate (3H—QNB), 1 ml of stored membranes is diluted to 30 ml and 0.1ml mixed with test compound and 0.27 nM (c. 25,000 cpm) 3H—QNB (Amersham International). For 3H—OXO—M, 1ml of membranes is diluted to 6 ml and 0.1 ml mixed with test compound and 2 nM (c. 250,000 cpm) 3H—OXO—M (New England Nuclear).

Non-specific binding of 3H—QNB is defined using 1 μM Atropine sulphate (2 μM Atropine) and of 3H—OXO—M using 10μM Oxotremorine. Non-specific binding values typically are 5% and 25% of total binding, respectively. Incubations are carried out at 37° C. for 30 min and the samples filtered using Whatman GF/B filters. (In the 3H—OXO—M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H—OXO—M and the muscarinic antagonist 3H—QNB. The ratio IC$_{50}$(3H—QNB)/IC$_{50}$(3H—OXO—M) gives an indication of the agonist character of the compound. Agonists typically exhibit a large ratio; antagonists typically exhibit a ratio near to unity.

The results are shown in Table 1.

TABLE 1

| Compound | [3H]-OXO-M IC$_{50}$(nM) | [3H]-QNB IC$_{50}$ (nM) |
|---|---|---|
| E3 | 14 | 6700 |
| E6 | 42 | 29000 |
| E10 | 17 | 4000 |
| E11 | 93 | 14000 |
| E12 | 145 | 15000 |
| E13 | 39 | 9400 |
| E14 | 160 | 9000 |
| E15 | 130 | 7800 |
| E17 | 230 | 48000 |
| E21 | 34 | 3800 |

We claim:

1. A compound of formula (I) or a pharmaceutically acceptable salt thereof:

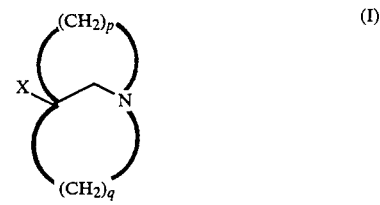

in which X represents R$_1$OOC— in which R$^1$ is C$_{1-4}$ alkyl, C$_{2-4}$ alkenyl or C$_{2-4}$ alkynyl; R$_2$O— in which R$_2$ is C$_{1-2}$ alkyl, C$_{1-2}$ alkylcarbonyl or aminocarbonyl optionally substituted by one or two methyl groups;

a group

in which Y represents a 3-membered divalent residue completing a 5-membered aromatic ring and comprises one or two heteroatoms selected from oxygen, nitrogen and sulphur, any amino nitrogen optionally substituted by a C$_{1-2}$ alkyl group, Y being optionally C-substituted by a methyl group; or a group

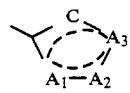

in which A$_1$ is oxygen or sulphur, one of A$_2$ and A$_3$ is CR$_3$ and the other is nitrogen or CR$_4$ where R$_3$ and R$_4$ are independently selected from hydrogen and methyl; and each of p=2 and q=3.

2. A compound according to claim 1, in which X represents a group

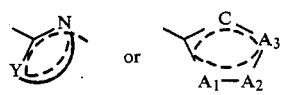

in which the variables are as defined in claim 1.

3. A compound according to claim 2 of formula (IA):

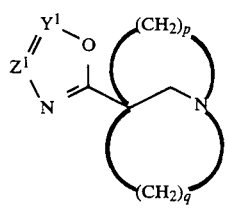

(IA)

wherein one of $Y^1$ and $Z^1$ represents $CR_5$, where $R_5$ is hydrogen or methyl, or nitrogen, and the other represents $CR_6$ where $R_6$ is hydrogen or a methyl group, and the remaining variables are as defined in claim 2.

4. A compound according to claim 3 in which X is selected from 3-methyl-1,2,4-oxadiazol-5-yl, 5-(H or methyl)-1,3,4-oxadiazol-2-yl and 4-(H or methyl)-5-(H or methyl)-1,3-oxazol-2-yl.

5. A compound according to claim 2 of formula (IB):

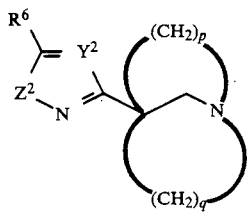

(IB)

wherein $Y^2$ is nitrogen or CH, $Z^2$ is oxygen or $NR_7$ where $R_7$ is hydrogen or $C_{1-2}$, and $R_6$ is hydrogen or methyl, and the remaining variables are as defined in claim 2.

6. A compound according to claim 5 in which X is selected from 5-methyl-1,2,4-oxadiazol-3-yl and 5-(H or methyl)-1,2-oxazol-3-yl.

7. A compound according to claim 2 of formula (IC):

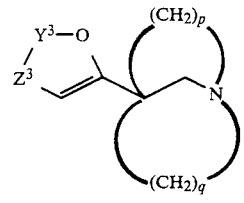

(IC)

wherein one of $Y^3$ and $Z^3$ is $CR_3$ and the other is $CR_4$, and $R_3$, $R_4$, p and q are as defined in claim 2.

8. A compound according to claim 7 in which X is selected from 2-furyl and 5-methylfur-2-yl.

9. A compound according to claim 1 other than methyl 1-azabicyclo[3.2.1]oct-5-ylcarboxylate.

10. A compound selected from the following 5-ethoxy-1-azabicyclo[3.2.1]octane,
1-azabicyclo[3.2.1]oct-5yl acetate,
ethyl 1-azabicyclo[3.2.1]oct-5-ylcarboxylate,
5-(3-methyl-1,2,4-oxadiazol-5yl)-1-azabicyclo
5-(1,3-oxazol-2-yl)-1-azabicyclo[3.2.1]octane, 5-(2-methyl-1,3,4-oxadiazol-5yl)-1-azabicyclo [3.2.1]octane,
5-(1,3,4-oxadiazol-2yl)-1-azabicyclo[3.2.1]octane,
5-(1,2-oxazol-5yl)-1-azabicyclo[3.2.1]octane, 5-(5-methyl-1,2,4-oxadiazol-3-yl)-1-azabicyclo [3.2.1]octane,
5-(fur-2-yl)-1-azabicyclo[3.2.1]octane,
5-(5-methylfur-2-yl)-1-azabicyclo[3.2.1]octane,
5-(5-methyl-1,2-oxazol-3-yl)-1-azabicyclo [3.2.1]octane,
5-(1,3,4-thiadiazol-2-yl)-1-azabicyclo[3.2.1]octane,
5-(2-methyl-1,3-oxazol-4-yl)-1-azabicyclo 3.2.1]octane or
5-(2-methyl-1,3-oxazol-5-yl)-1-azabicyclo 3.2.1]octane, or a pharmaceutically acceptable salt thereof.

11. A pharmaceutical composition for the treatment or prophylaxis of dementia which comprises a therapeutically effective amount of the compound according to claim 1 and a pharmaceutically acceptable carrier.

12. A method of treatment and/or prophylaxis of dementia in mammals including humans, which comprises administering to the sufferer an effective amount of a compound according to claim 1.

* * * * *

UNITED STATES PATENT AND TRADEMARK OFFICE
CERTIFICATE OF CORRECTION

PATENT NO. : 4,971,975
DATED : November 20, 1990
INVENTOR(S) : Michael S. Hadley; Paul A. Wyman; Barry S. Orlek It is certified that error appears in the above-identified patent and that said Letters Patent is hereby corrected as shown below:

Column 42, line 56, delete "each of".

Column 43, line 35, after "$C_{1-2}$" add --alkyl--.

Column 44, line 19, change "1-azabicyclo[3.2.1]oct-5yl" to --1-azabicyclo[3.2.1]oct-5-yl--;
    line 21, change "5-(3-methyl-1,2,4-oxadiazol-5yl)-1-azabicyclo" to --5-(3-methyl-1,2,4-oxadiazol-5-yl)-1-azabicyclo[3.2.1]octane,--;
    lines 23-24, change "methyl-1,3,4-oxadiazol-5yl)-1-azabicyclo [3.2.1]oc-tane" to --methyl-1,3,4-oxadiazol-5-yl)-1-azabicyclo[3.2.1]octane--;
    line 25, change "5-(1,3,4-oxadiazol-2yl)-1-azabicyclo[3.2.1]octane," to --5-(1,3,4-oxadiazol-2-yl)-1-azabicyclo[3.2.1]octane,--;
    line 26, change "5-(1,2-oxazol-5yl)-1-azabicyclo[3.2.1]octane," to --5-(1,2-oxazol-5-yl)-1-azabicyclo[3.2.1]octane,; and
    line 32, change "5-(2-methyl-1,3-oxazol-4-yl)-1-azabicyclo 3.2.1]octane" to --5-(2-methyl-1,3-oxazol-4-yl)-1-azabicyclo[3.2.1]octane,--.

UNITED STATES PATENT AND TRADEMARK OFFICE
CERTIFICATE OF CORRECTION

PATENT NO. : 4,971,975

DATED : November 20, 1990

INVENTOR(S) : Michael S. Hadley; Paul A. Wyman; Barry S. Orlek

It is certified that error appears in the above-identified patent and that said Letters Patent are hereby corrected as shown below:

Column 44, formula (IC) should appear as:

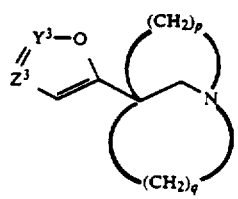

Signed and Sealed this

Eighth Day of December, 1992

Attest:

DOUGLAS B. COMER

*Attesting Officer*       *Acting Commissioner of Patents and Trademarks*